United States Patent
Jin

(10) Patent No.: US 10,390,793 B2
(45) Date of Patent: Aug. 27, 2019

(54) BACKING ELEMENT OF ULTRASONIC PROBE, BACKING LAYER OF ULTRASONIC PROBE, AND MANUFACTURING METHOD THEREOF

(71) Applicant: SAMSUNG MEDISON CO., LTD., Gangwon-Do (KR)

(72) Inventor: Gil-ju Jin, Seoul (KR)

(73) Assignee: Samsung Medison Co., Ltd., Gangwon-Do (KR)

( * ) Notice: Subject to any disclaimer, the term of this patent is extended or adjusted under 35 U.S.C. 154(b) by 994 days.

(21) Appl. No.: 13/756,317

(22) Filed: Jan. 31, 2013

(65) Prior Publication Data

US 2013/0197368 A1   Aug. 1, 2013

(30) Foreign Application Priority Data

Jan. 31, 2012 (KR) .................. 10-2012-0010064

(51) Int. Cl.
| | |
|---|---|
| *A61B 8/00* | (2006.01) |
| *A61B 8/13* | (2006.01) |
| *H04R 31/00* | (2006.01) |
| *B06B 1/06* | (2006.01) |

(52) U.S. Cl.
CPC .............. *A61B 8/4444* (2013.01); *A61B 8/13* (2013.01); *A61B 8/4488* (2013.01); *B06B 1/0681* (2013.01); *H04R 31/00* (2013.01); *Y10T 29/49005* (2015.01)

(58) Field of Classification Search
None
See application file for complete search history.

(56) References Cited

U.S. PATENT DOCUMENTS

| | | | |
|---|---|---|---|
| 5,640,370 A * | 6/1997 | Hanafy | B06B 1/0629 310/334 |
| 6,625,854 B1 | 9/2003 | Sudol et al. | |
| 2008/0098816 A1 | 5/2008 | Yamashita et al. | |
| 2008/0200812 A1 | 8/2008 | Osawa | |
| 2010/0234792 A1* | 9/2010 | Dacey, Jr. | A61L 2/0011 604/8 |

FOREIGN PATENT DOCUMENTS

| | | |
|---|---|---|
| EP | 0637470 A2 | 2/1995 |
| EP | 0637470 A3 | 11/1995 |
| JP | 2009-254447 A | 11/2009 |
| WO | 02/40184 A2 | 5/2002 |
| WO | 02/40184 A3 | 9/2002 |

OTHER PUBLICATIONS

Extended European Search Report issued in Application No. EP13153429.9, dated Sep. 21, 2017.

* cited by examiner

*Primary Examiner* — Joseph M Santos Rodriguez
(74) *Attorney, Agent, or Firm* — Morgan, Lewis & Bockius LLP

(57) ABSTRACT

A backing element of a ultrasonic probe, a backing layer of a ultrasonic probe, and a manufacturing method thereof, the backing layer formed by arranging a plurality of members each having a shape of a polygonal column in a one-dimensional manner or in a two-dimensional manner while each of the plurality of members is provided with a conductive trace formed at one side surface thereof, thereby electrically connecting an ultrasonic transducer array, which is being acoustically connected to the backing layer, in a further simple and definite manner.

20 Claims, 16 Drawing Sheets

(a)

(b)

(a)

(b)

(c)

(a)

(b)

(c)

(a)

(b)

(c)

(a)

(b)

(c)

(a)

(b)

(a)

(b)

(c)

(a)

(b)

(c)

BACKING ELEMENT OF ULTRASONIC PROBE, BACKING LAYER OF ULTRASONIC PROBE, AND MANUFACTURING METHOD THEREOF

CROSS-REFERENCE TO RELATED APPLICATION

This application claims the benefit of Korean Patent Application No. 10-2012-0010064, filed on Jan. 31, 2012, in the Korean Intellectual Property Office, the disclosure of which is incorporated herein by reference.

BACKGROUND

1. Field

Embodiments of the present disclosure relate to an ultrasonic probe configured to generate an image of an inside a subject by using an ultrasonic wave.

2. Description of the Related Art

An ultrasonic diagnostic apparatus is an apparatus configured to scan an ultrasonic signal toward a desired portion at an inside a body of a subject from a surface of a body of the subject, and to obtain an image through a non-invasive measurement with respect to a cross section of a soft tissue or a blood flow by using the information of the ultrasonic signal, that is, an ultrasonic echo signal, that is reflected. The apparatus as such, when compared to other image diagnostic apparatus such as an x-ray diagnostic apparatus, an x-ray CT scanner (a Computerized Tomography scanner), a MRI (a Magnetic Resonance Image), or a nuclear medicine diagnostic apparatus, is small-sized and inexpensive, while capable of displaying an image in real time, and since no radiation exposure of x-ray is present, a high level of safety is provided, and thus the apparatus as such is widely used in the diagnosis of a heart, a stomach, and an urinary system, as well as in the diagnosis of gynecology.

Particularly, the ultrasonic diagnostic apparatus includes an ultrasonic probe configured to transmit an ultrasonic signal to a subject to obtain an ultrasonic image of the subject, and to receive the ultrasonic echo signal being reflected from the subject.

The ultrasonic probe includes a piezo-electric layer configured to reciprocally change an electrical signal and an acoustic signal while piezo-electric material is vibrated, a matching layer configured to decrease a difference of acoustic impedance in between the piezo-electric layers and a subject so that the ultrasonic wave generated at the piezo-electric layer may be delivered to the subject as much as possible, a len layers configured to gather the ultrasonic wave proceeding toward a front of the piezo-electric layer to a particular point, a transducer module having an acoustic absorption layer, that is, a backing layer, that prevent an image distortion by blocking the ultrasonic wave from proceeding toward a rear of the piezo-electric layer, a case having an upper portion thereof open, and a cover configured to make contact with a surface of the subject while being coupled to the upper portion of the case having an opening thereof.

The ultrasonic diagnostic apparatus is configured to obtain a cross-sectional image of a subject by scanning an ultrasonic wave at an inside the subject, and detecting the reflection of the ultrasonic wave. The ultrasonic diagnostic apparatus as such includes a mechanical scanning method configured to scan an ultrasonic wave by moving an ultrasonic probe in a mechanical manner, and an electronic scanning method configured to scan an ultrasonic wave by a control of the electronic change and the delayed time by using an array oscillator, that is, an ultrasonic transducer array.

A conventional ultrasonic diagnostic apparatus is generally configured to scan an ultrasonic beam to an inside a single surface, and thus is composed of a system configured to display a cross section, that is, a plane surface image. However, in recent years, an attempt to obtain three-dimensional information by collecting a diagnostic image while moving an ultrasonic probe, which is an ultrasonic transmission/reception unit of an ultrasonic diagnostic apparatus is being frequently made, and a displaying of a three-dimensional image with respect to an ultrasonic diagnostic apparatus is expected to lead to a possibility of a new diagnosis.

Particularly, a two-dimensional ultrasonic transducer array and a two-dimensional array system provided with an objective to obtain three-dimensional image information, by arranging ultrasonic transducer elements (oscillators) that compose the piezo-electric layer of the ultrasonic probe in a two-dimensional manner and by scanning beam at a diagnostic domain in a three-dimensional manner through the control of the electronic change and the delayed time, is being researched.

By using the ultrasonic transducers employed with the two-dimensional array system as such, when compared to a system configured to mechanically move the ultrasonic transducer, a collection of three-dimensional information may be able to be performed within a short period of time, and the real-time processing performance may be remarkably enhanced.

When manufacturing the two-dimensional transducer array being used at the two-dimensional array system as such, the ultrasonic transducer elements are arranged in a two-dimensional manner while having a microscopic distance in between the ultrasonic transducer elements so that an ultrasonic wave may be deflected toward a predetermined direction. At this time, from each of the ultrasonic transducer elements arranged in a two-dimensional manner, an electrode lead wire electrically connected is needed to be withdrawn.

However, since the number of the ultrasonic transducer elements being arranged at the two-dimensional transducer array is in thousands of units, the withdrawal of the electrode lead wire from the each of the ultrasonic transducer elements is practically difficult, and even in a case when the electrode lead wire is withdrawn from the each of the ultrasonic transducer elements, a many number of electrode lead wires being withdrawn may be tangled at an inside a narrow space of the piezo-electric layers, and thus a composition of a circuit is being complicated.

SUMMARY

Therefore, it is an aspect of the present disclosure to provide a backing element of an ultrasonic probe, configured in a way that each of a plurality of ultrasonic transducer elements that composes an ultrasonic transducer array is electrically connected in a further simple and definite manner, a backing layer of a ultrasonic probe, and a manufacturing method thereof.

It is another aspect of the present disclosure to provide a backing element of an ultrasonic probe configured to enhance electrical characteristics in a case when electrically connecting a plurality of ultrasonic transducer elements that composes an ultrasonic transducer array, a backing layer of the ultrasonic probe, and a manufacturing method thereof.

Additional aspects of the disclosure will be set forth in part in the description which follows and, in part, will be obvious from the description, or may be learned by practice of the disclosure.

In accordance with one aspect of the present disclosure, a backing element of an ultrasonic probe includes a member having a shape of a polygonal column and a conductive trace. The member may be acoustically connected to an ultrasonic transducer element. The conductive trace may be formed at one side surface of the member and electrically connected to the ultrasonic transducer element.

An electrode layer may be formed at an upper surface or a lower surface of the member, the upper surface or the lower surface being acoustically connected to the ultrasonic transducer element.

In accordance with another aspect of the present disclosure, a backing element of an ultrasonic probe includes a member having a shape of a polygonal column, and conductive traces. The member may be acoustically connected to an ultrasonic transducer element. The conductive traces may be formed at more than two side surfaces of the member and electrically connected to the ultrasonic transducer element.

An electrode layer may be formed at an upper surface or a lower surface of the member, the upper surface or the lower surface being acoustically connected to the ultrasonic transducer element.

In accordance with another aspect of the present disclosure, a backing layer of an ultrasonic probe includes a plurality of members each having a shape of a polygonal column arranged in a one-dimensional manner or in a two-dimensional manner, the plurality of members each provided at one side surface thereof with a conductive trace. The plurality of members may be acoustically connected to a ultrasonic transducer array, and each of the conductive traces formed at each of the plurality of members may be electrically connected to one of a plurality of ultrasonic transducer elements that composes the ultrasonic transducer array.

An electrode layer may be formed at an upper surface or a lower surface of the member, the upper surface or the lower surface being acoustically connected to the ultrasonic transducer array.

The plurality of members may be adhesively attached to each other by using same material as material of the member, and may be arranged in a one-dimensional manner or in a two-dimensional manner.

In accordance with another aspect of the present disclosure, a backing layer of an ultrasonic probe includes a plurality of members each having a shape of a polygonal column arranged in a one-dimensional manner or in a two-dimensional manner, the plurality of members each provided at more than two side surfaces thereof with conductive traces formed. The plurality of members may be acoustically connected to a ultrasonic transducer array, and each of the conductive traces formed at each of the plurality of members may be electrically connected to one of a plurality of ultrasonic transducer elements that composes the ultrasonic transducer array.

An electrode layer may be formed at an upper surface or a lower surface of the member, the upper surface or the lower surface being acoustically connected to the ultrasonic transducer array.

The plurality of members may be adhesively attached to each other by using same material as material of the member, and may be arranged in a one-dimensional manner or in a two-dimensional manner.

In accordance with another aspect of the present disclosure, a method of manufacturing a backing element of an ultrasonic probe is as follows. A member having a shape of a polygonal column while being acoustically connected to an ultrasonic transducer element may be generated. A conductive trace may be formed at one side surface of the member, the conductive trace being electrically connected to the ultrasonic transducer element.

The method may be achieved by further performing follows. An electrode layer may be formed at an upper surface or a lower surface of the member, the upper surface or the lower surface being acoustically connected to the ultrasonic transducer element.

In accordance with another aspect of the present disclosure, a method of manufacturing a backing element of an ultrasonic probe is as follows. A member having a shape of a polygonal column while being acoustically connected to an ultrasonic transducer element may be generated. Conductive traces may be formed at more than two side surfaces of the member, the conductive traces each electrically connected to the ultrasonic transducer element.

The method may be achieved by further performing follows. An electrode layer may be formed at an upper surface or a lower surface of the member, the upper surface or the lower surface being acoustically connected to the ultrasonic transducer element.

In accordance with another aspect of the present disclosure, a method of manufacturing a backing layer of an ultrasonic probe is as follows. A plurality of members each having a shape of a polygonal column while being acoustically connected to an ultrasonic transducer array may be generated. A conductive trace may be formed at one side surface of each of the plurality of members, each of the conductive traces being electrically connected to one of a plurality of ultrasonic transducer elements that composes the ultrasonic transducer array. The plurality of members each provided with the conductive trace formed may be arranged in a one-dimensional manner or in a two-dimensional manner.

The method may be achieved by further performing follows. An electrode layer may be formed at an upper surface or a lower surface of the member, the upper surface or the lower surface being acoustically connected to the ultrasonic transducer array.

The arranging of the plurality of members in a one-dimensional manner or in a two-dimensional manner may include adhesively attaching the plurality of members each other by using same material as material of the member.

In accordance with another aspect of the present disclosure, a method of manufacturing a backing layer of an ultrasonic probe is as follows. A plurality of member each having a shape of a polygonal column while being acoustically connected to an ultrasonic transducer array may be generated. Conductive traces may be formed at more than two side surfaces of each of the plurality of members, each of the conductive traces electrically connected to one of a plurality of ultrasonic transducer elements that composes the ultrasonic transducer array. The plurality of members each provided with the conductive trace formed thereof may be arranged in a one-dimensional manner or in a two-dimensional manner.

The method may be achieved by further performing follows. An electrode layer may be formed at an upper surface or a lower surface of the member, the upper surface or the lower surface being acoustically connected to the ultrasonic transducer array.

The arranging of the plurality of members in a one-dimensional manner or in a two-dimensional manner may include adhesively attaching the plurality of members each other by using same material as material of the member.

In accordance with another aspect of the present disclosure, a backing element of an ultrasonic probe includes a member having a shape of a hexagonal column and a conductive trace. The member may be acoustically connected to an ultrasonic transducer element. The conductive trace may be formed at one side surface of the member and electrically connected to the ultrasonic transducer element.

An electrode layer may be formed at an upper surface or a lower surface of the member, the upper surface or the lower surface being acoustically connected to the ultrasonic transducer element.

In accordance with another aspect of the present disclosure, a backing element of an ultrasonic probe includes a member having a shape of a hexagonal column and conductive traces. The member may be acoustically connected to an ultrasonic transducer element. Conductive traces may be formed at more than two side surfaces of the member and electrically connected to the ultrasonic transducer element.

An electrode layer may be formed at an upper surface or a lower surface of the member, the upper surface or the lower surface being acoustically connected to the ultrasonic transducer element.

In accordance with another aspect of the present disclosure, a backing layer of an ultrasonic probe includes a plurality of members each having a shape of a hexagonal column arranged in a one-dimensional manner or in a two-dimensional manner, the plurality of members each provided at more than two side surfaces thereof with conductive traces. The plurality of members may be acoustically connected to an ultrasonic transducer array, and each of the conductive traces formed at each of the plurality of members is electrically connected to one of a plurality of ultrasonic transducer elements that composes the ultrasonic transducer array.

In accordance with another aspect of the present disclosure, a backing element of an ultrasonic probe includes a member having a shape of a triangular column and a conductive trace. The member may be acoustically connected to an ultrasonic transducer element. The conductive trace may be formed at one side surface of the member and electrically connected to the ultrasonic transducer element.

An electrode layer may be formed at an upper surface or a lower surface of the member, the upper surface or the lower surface being acoustically connected to the ultrasonic transducer element.

In accordance with another aspect of the present disclosure, a backing element of an ultrasonic probe includes a member having a shape of a triangular column and conductive traces. The member may be acoustically connected to an ultrasonic transducer element. The conductive traces may be formed at more than two side surfaces of the member and electrically connected to the ultrasonic transducer element.

An electrode layer may be formed at an upper surface or a lower surface of the member, the upper surface or the lower surface being acoustically connected to the ultrasonic transducer element.

In accordance with another aspect of the present disclosure, a backing layer of an ultrasonic probe includes a plurality of members each having a shape of a triangular column arranged in a one-dimensional manner or in a two-dimensional manner, the plurality of member each provided at more than two side surfaces thereof with conductive traces. The plurality of members may be acoustically connected to an ultrasonic transducer array, and each of the conductive trace formed at each of the plurality of members is electrically connected to one of a plurality of ultrasonic transducer elements that composes the ultrasonic transducer array.

As described above, by forming a backing layer of an ultrasonic probe by arranging a plurality of polygonal column shape members in a one-dimensional manner or in a two-dimensional manner, each of the plurality of polygonal column shape members provided at one side surface thereof with a conductive trace, an ultrasonic transducer array being acoustically connected to the backing layer of the ultrasonic probe is be electrically connected in a further simple and definite manner.

In addition, by forming a backing layer of an ultrasonic probe by arranging a plurality of polygonal column shape members in a one-dimensional manner or in a two-dimensional manner, each of the plurality of members provided at more than two side surfaces thereof with a conductive trace, an electrical characteristic may be enhanced in a case when an ultrasonic transducer array being acoustically connected to the backing layer of the ultrasonic probe is electrically connected.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
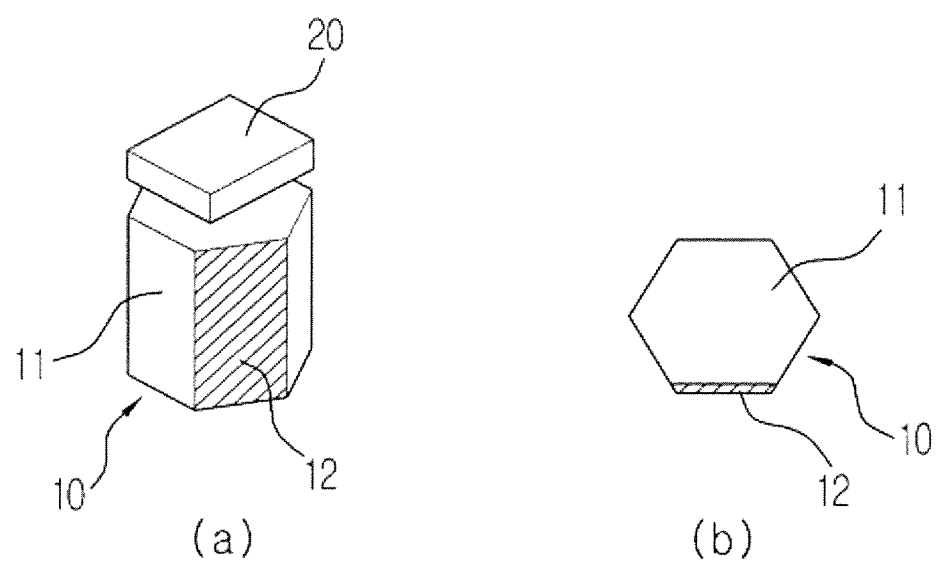
FIG. 1 illustrates a perspective view and a cross-sectional view of a backing element of an ultrasonic probe in accordance with the first embodiment of the present disclosure.

Reference will now be made in detail to the embodiments of the present disclosure, examples of which are illustrated in the accompanying drawings, wherein like reference numerals refer to like elements throughout.

FIG. 1 illustrates a perspective view and a cross-sectional view of a backing element of an ultrasonic probe in accordance with the first embodiment of the present disclosure.

As illustrated on (a) of FIG. 1, a backing element 10 of an ultrasonic probe in accordance with the first embodiment of the present disclosure includes a member 11 having a shape of a polygonal column and a conductive trace 12 formed at one side surface of the member 11. On FIG. 1, as the member 11 having a shape of a polygonal column, the member having a shape of a hexagonal column from various polygonal columns is provided as an example. The backing element 10, or a portion thereof, may also be described as a member.

The backing element 10 illustrated on (a) of FIG. 1, becomes a basic component of a backing layer that is configured to absorb an ultrasonic wave, which is radiated toward a rear of a piezo-electric layer by the resonance of a piezo-electric element (oscillator) that composes the piezo-electric layer at an inside a transducer module. Here, the member 11 having a shape of a polygonal column is manufactured by synthetic material composed of epoxy resin, tungsten, and rubber powder, and other than the synthetic material as such, any material suitable for absorbing rear sound caused by the resonance of piezo-electric material may be used in manufacturing the member 11 having a shape of a polygonal column.

As illustrated on (a) of FIG. 1, at one side surface of the member 11 having a shape of a hexagonal column while provided with six units of side surfaces thereof, the conductive trace 12 is formed. Here, the forming of the conductive trace 12 is referred to as adding (plastering) electrical contact point material on a side surface of the member 11 having a shape of a polygonal column by using various adjustment synthesis techniques. When forming the conductive trace 12, as the electrical contact point material, metals, graphite corresponding to conductive material, or conductive ink may be used, and as a method of adding electrical contact point material on a side surface of the member 11 having a shape of a polygonal column, a technique such as a laser scribing, a planting, a deposition, or a printing may be applied.

The backing element 10 is electrically and acoustically connected to one ultrasonic transducer element 20. The ultrasonic transducer element 20 is generally composed of PZT (Lead Zirconium Titanite Ceramics) or a MUT (Micromachined Ultrasonic Transducer). As to describe the electrical and acoustic connection between the backing element 10 and the ultrasonic transducer element 20 in more detail, the member 11 that composes the backing element 10 while having a shape of a polygonal column is acoustically connected to the one ultrasonic transducer element 20 by making contact with the one ultrasonic transducer element 20, and weakens or absorbs acoustic energy that is being radiated from a rear surface of the ultrasonic transducer element 20. In addition, the conductive trace 12 formed at one side surface of the member 11 having a shape of a polygonal column is electrically connected to the one ultrasonic transducer element 20, and electrically connects the ultrasonic transducer element 20.

(b) of FIG. 1 shows a cross section of the backing element 10, and illustrates an image of the conductive trace 12 formed only at one side surface of the member 11 having a shape of a hexagonal column provided with six units of side surfaces thereof.

Figure 2:
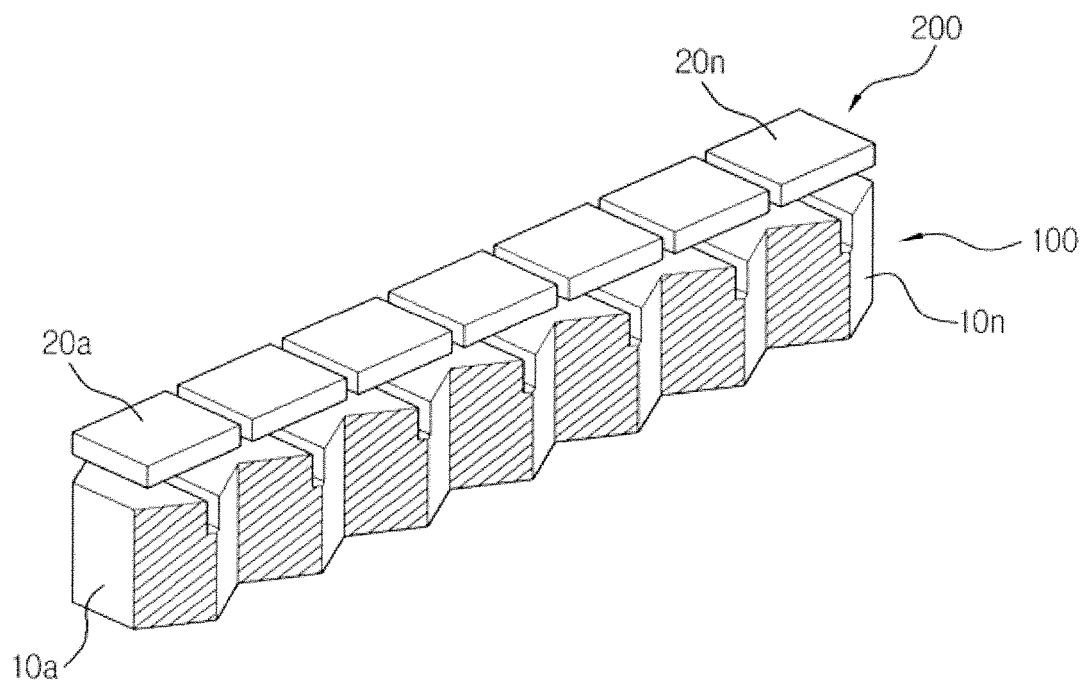
FIG. 2 is a perspective view of a backing layer of the ultrasonic probe formed by arranging the backing elements of the ultrasonic probe in a one-dimensional manner in accordance with the first embodiment of the present disclosure.

FIG. 2 is a perspective view of a backing layer of the ultrasonic probe formed by arranging the backing elements of the ultrasonic probe in a one-dimensional manner in accordance with the first embodiment of the present disclosure.

The backing element 10, which is same as the backing element 10 illustrated on (a) of FIG. 1, is provided in plurality units (a 'n' number of the backing element 10), and by arranging a plurality of backing elements 10a to 10n in a one-dimensional manner, that is, in a linear manner, a backing layer 100 is formed as illustrated on FIG. 2.

As illustrated on FIG. 2, at the backing layer 100 formed by arranging the plurality (the 'n' number) of the backing elements 10a to 10n in a one-dimensional manner, a one-dimensional ultrasonic transducer array 200 formed by arranging a plurality (a 'm' number) of ultrasonic transducer elements 20a to 20m in a one-dimensional manner is electrically and acoustically connected. As to describe the electrical and acoustic connection between the backing layer 100 and the one-dimensional ultrasonic transducer array 200 in more detail, the plurality of members 11a to 11n having a shape of a polygonal column that compose the backing layer 100 are acoustically connected to the one-dimensional ultrasonic transducer array 200 by making contact with the one-dimensional ultrasonic transducer array 200, and weakens or absorbs acoustic energy that is being radiated from a rear surface of the one-dimensional ultrasonic transducer array 200. In addition, conductive traces 12a to 12n each formed at each of the members 11a to 11n having a shape of a polygonal column is electrically connected to one of the plurality (the 'm' number) of the ultrasonic transducer elements 20a to 20n that composes the one dimensional ultrasonic transducer array 100, and electrically connects the ultrasonic transducer elements 20a to 20n. Although not illustrated on FIG. 2, the backing layer 100 of the ultrasonic probe is mounted at a printed circuit board (not shown), and the conductive traces 12a to 12n each formed at each of the members 11a to 11n having a shape of a polygonal column forming the backing layer 100 is electrically connected to a conductive trace formed at the printed circuit board, and electrically connects each of the ultrasonic transducer elements 20a to 20n.

Figure 3:
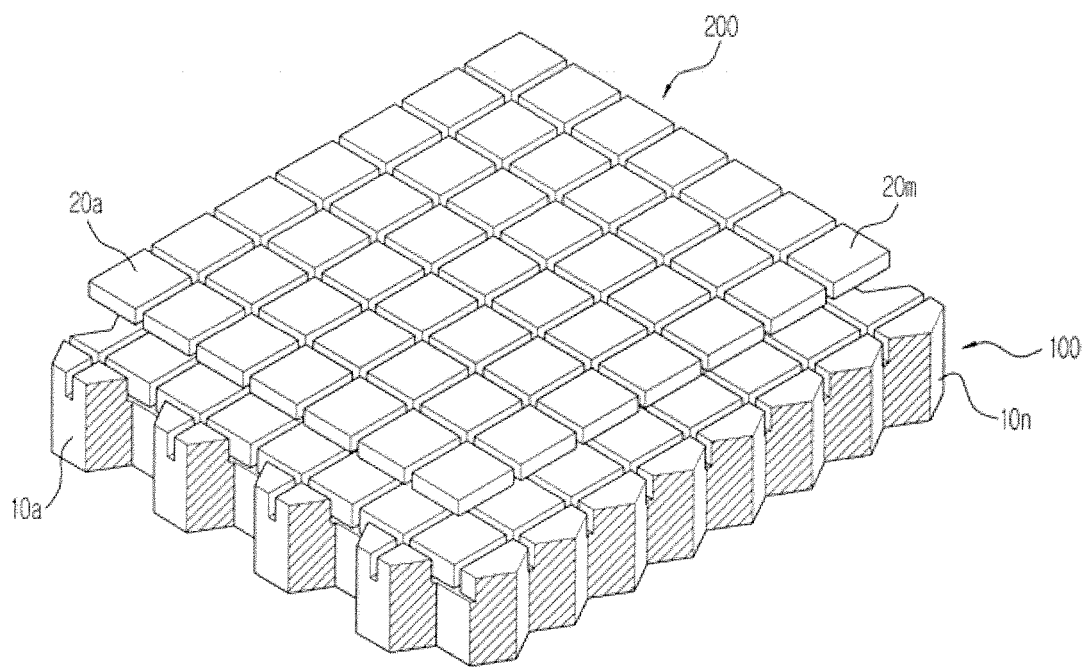
FIG. 3 is a perspective view of a backing layer of the ultrasonic probe formed by arranging the backing elements of the ultrasonic probe in a two-dimensional manner in accordance with the first embodiment of the present disclosure.

FIG. 3 is a perspective view of a backing layer of the ultrasonic probe formed by arranging the backing elements of the ultrasonic probe in a two-dimensional manner in accordance with the first embodiment of the present disclosure.

The backing element 10, which is same as the backing element 10 illustrated on (a) of FIG. 1, is provided in plurality units (a 'n' number of the backing element 10), and by arranging a plurality of backing elements 10a to 10n in a two-dimensional manner, that is, in a plane manner, the backing layer 100 is formed as illustrated on FIG. 3.

As illustrated on FIG. 3, at the backing layer 100 formed by arranging the plurality (the 'n' number) of the backing elements 10a to 10n in a two-dimensional manner, a two-dimensional ultrasonic transducer array 200 formed by arranging a plurality (a 'm' number) of ultrasonic transducer elements 20a to 20m in a two-dimensional manner is electrically and acoustically connected. As to describe the electrical and acoustic connection between the backing layer 100 and the two-dimensional ultrasonic transducer array 200 in detail, a plurality of members 11a to 11n having a shape of a polygonal column that compose the backing layer 100 are acoustically connected to the two-dimensional ultrasonic transducer array 200 by making contact with the two-dimensional ultrasonic transducer array 200, and weakens or absorbs acoustic energy that is being radiated from a rear surface of the two-dimensional ultrasonic transducer array 200. In addition, conductive traces 12a to 12n each formed at each of the members 11a to 11n having a shape of a polygonal column is electrically connected to one of the plurality (the 'm' number) of the ultrasonic transducer elements 20a to 20m, and electrically connects the ultrasonic transducer elements 20a to 20m. Although not illustrated on FIG. 3, the backing layer 100 of the ultrasonic probe is mounted at a printed circuit board (not shown), and the conductive traces 12a to 12n each formed at each of the members 11a to 11n having a shape of a polygonal column forming the backing layer 100 is electrically connected to a conductive trace formed at the printed circuit board, and electrically connects each of the ultrasonic transducer elements 20a to 20m.

Figure 4:
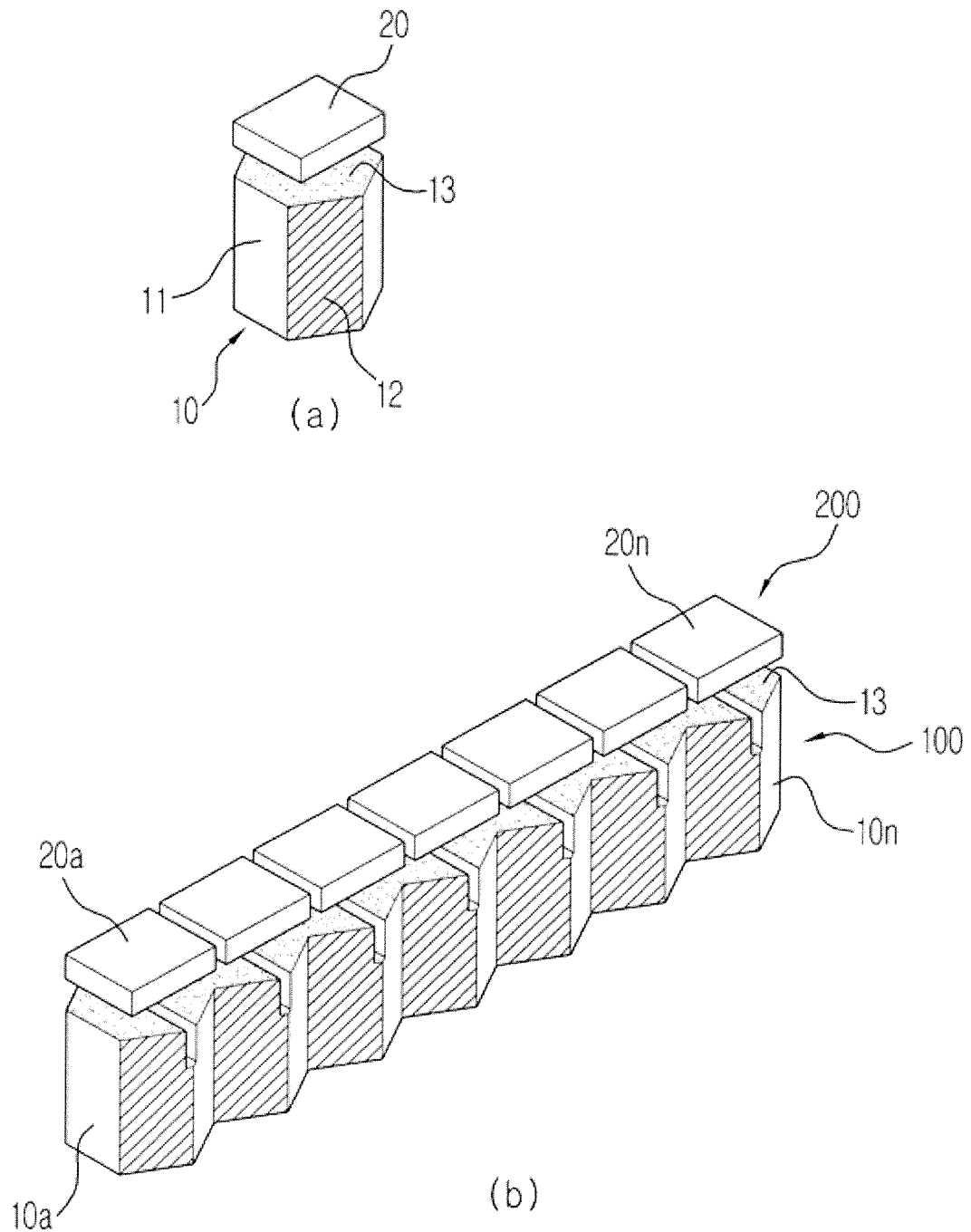
FIG. 4 illustrates a perspective view of a backing element of an ultrasonic probe in accordance with the second embodiment of the present disclosure, and a perspective view of a backing layer of the ultrasonic probe formed by arranging the backing elements of the ultrasonic probe in a one-dimensional manner in accordance with the second embodiment of the present disclosure.

FIG. 4 illustrates a perspective view of a backing element of an ultrasonic probe in accordance with the second embodiment of the present disclosure, and a perspective view of a backing layer of the ultrasonic probe formed by arranging the backing elements of the ultrasonic probe in a one-dimensional manner in accordance with the second embodiment of the present disclosure.

As illustrated on (a) of FIG. 4, the backing element 10 of an ultrasonic probe in accordance with the second embodiment of the present disclosure, which is provided with an electrode layer 13 further formed at an upper surface or at a lower surface of the member 11 that is acoustically connected to the ultrasonic transducer element 20, is different from the backing element 10 illustrated on (a) of FIG. 1. As the above, when the electrode layer 13 is formed at an upper surface or at a lower surface of the member 11 acoustically connected to the ultrasonic transducer element 20, the electrical connection between the ultrasonic transducer element 20 and the conductive trace 12 formed at a side surface of the member 11 having a shape of a polygonal column may be further enhanced.

The backing element 10, which is same as the backing element 10 illustrated on (a) of FIG. 4, is provided in plurality units (a 'n' number of the backing element 10), and by arranging a plurality of backing elements 10a to 10n in a one-dimensional manner, that is, in a linear manner, the backing layer 100 is formed as illustrated on (b) of FIG. 4.

With respect to the structure of a circuit of the backing layer 100 of the ultrasonic probe formed by arranging the backing elements in a one-dimensional manner in accordance with the second embodiment of the present disclosure as illustrated on (b) of FIG. 4, other than the structure of the electrode layer 13 formed at an upper surface or at a lower surface of the member 11 having a shape of a polygonal column, since all other components are same as the structure of the backing layer 100 of an ultrasonic probe formed by arranging the backing elements of an ultrasonic probe in a one-dimensional manner in accordance with the second embodiment of the present disclosure as illustrated on FIG. 2, the detailed description as such will be omitted.

Figure 5A:
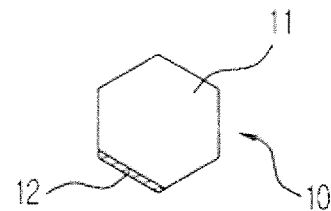
FIG. 5A is a cross-sectional view provided to describe the backing element of the ultrasonic probe in accordance with the first embodiment of the present disclosure in a case when a conductive trace is formed only at one side surface of the member having a shape of a polygonal (hexagonal) column that forms the backing element of the ultrasonic probe, the backing layer of the ultrasonic probe formed by arranging the backing elements of the ultrasonic probe in a one-dimensional manner, and the backing layer of the ultrasonic probe formed by arranging the backing elements of the ultrasonic probe in a two-dimensional manner.
Figure 5A:
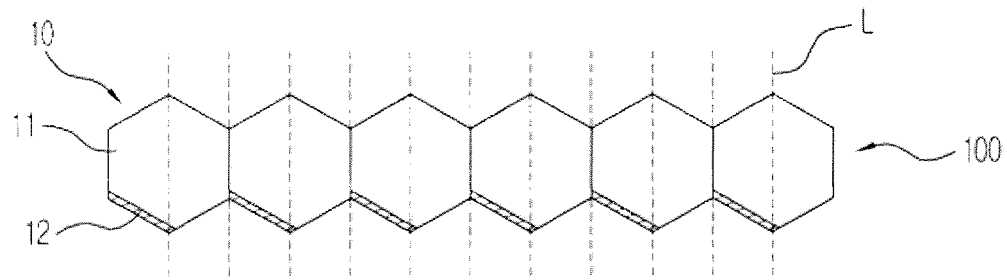
Figure 5A:
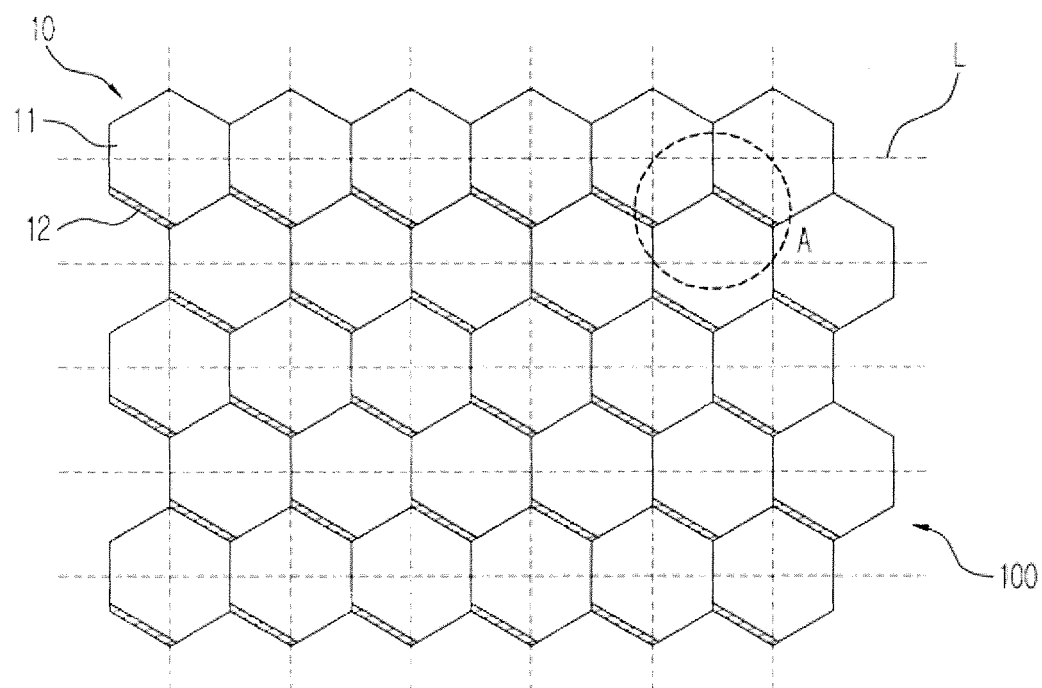

(a) of FIG. 5A is a cross-sectional view of the backing element 10 having the member 11 having a shape of a polygonal (hexagonal) column and the conductive trace 12 formed at one side surface of the member 11 having a shape of a hexagonal column, (b) of FIG. 5A is a cross-sectional view of the backing layer 100 formed by arranging the backing elements 10 illustrated at (a) of FIG. 5A in a one-dimensional manner, and (c) of FIG. 5A is a cross-sectional view of the backing layer 100 formed by arranging the backing elements 10 illustrated at the (a) of FIG. 5A in a two-dimensional manner. The straight line illustrated with a dotted line on FIG. 5A is referred to as a dicing line 'L'. At a domain (a curvature domain illustrated with dotted line at (c) of FIG. 5A, that is, the "A" domain) divided by the dicing line 'L', one ultrasonic transducer element is connected.

At the above, a case of the forming of the backing layer 100, which is performed by arranging the members 11 having a shape of a polygonal column in a one-dimensional manner or in a two-dimensional manner while each of the members 11 having a shape of a polygonal column is provided with the conductive trace 12 formed only at one side surface thereof, has been described, but hereinafter, by referring to FIG. 5B, a case of the forming of the backing layer 100, which is performed by arranging the members 11 having a shape of a polygonal column in a one-dimensional manner or in a two-dimensional manner while each of the members 11 having a shape of a polygonal column is provided with the conductive traces 12 formed at two side surfaces thereof, will be described.

Figure 5B:
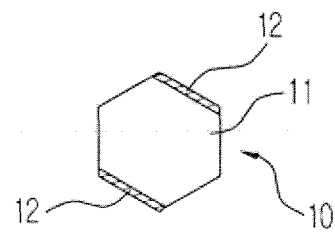
FIG. 5B is a cross-sectional view provided to describe the backing element of the ultrasonic probe in accordance with the first embodiment of the present disclosure in a case when conductive traces are formed at two side surfaces of the member having a shape of a polygonal (hexagonal) column that forms the backing element of the ultrasonic probe, the backing layer of the ultrasonic probe formed by arranging the backing elements of the ultrasonic probe in a one-dimensional manner, and the backing layer of the ultrasonic probe formed by arranging the backing elements of the ultrasonic probe in a two-dimensional manner.
Figure 5B:
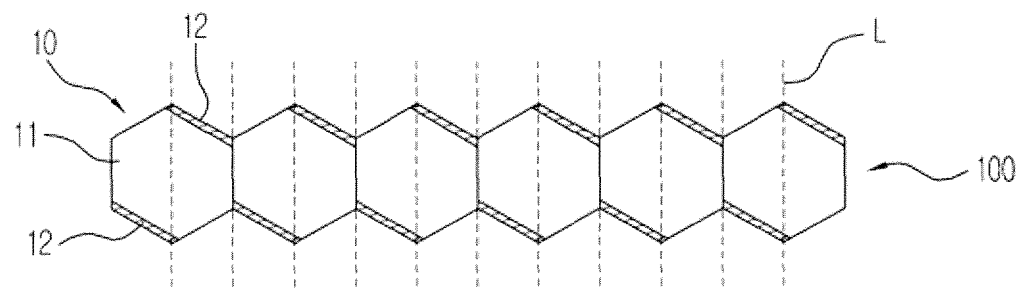
Figure 5B:
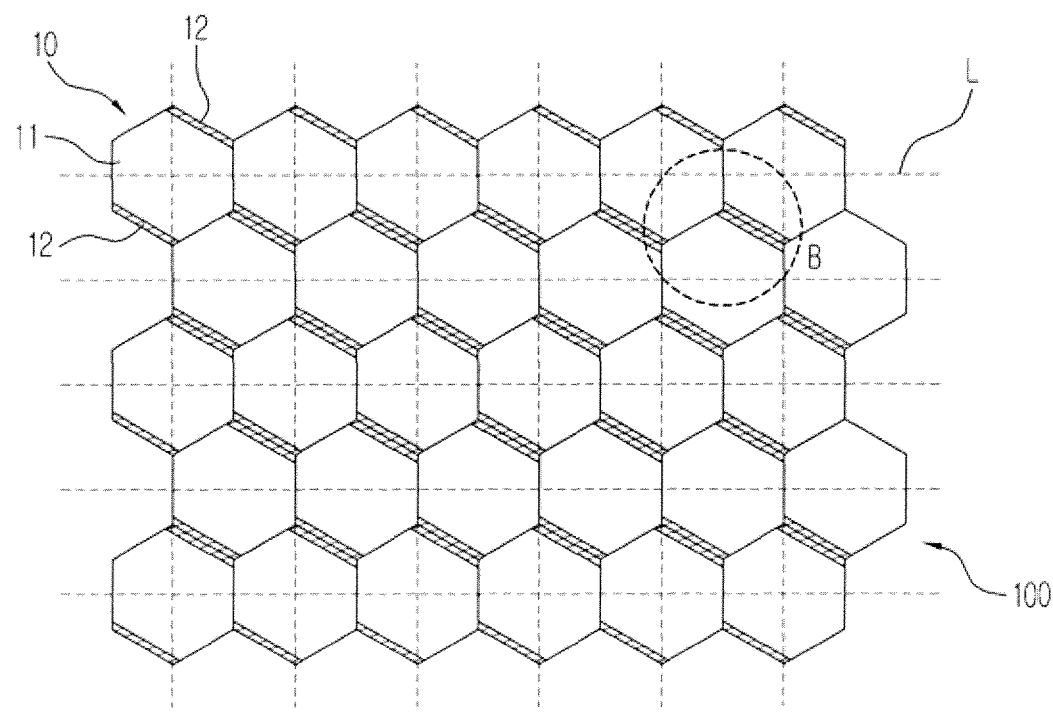

(a) of FIG. 5B is a cross-sectional view of the backing element 10 that includes the member 11 having a shape of a polygonal (hexagonal) column and also includes the conductive traces 12 formed at two side surfaces of the member 11 having a shape of a hexagonal column, (b) of FIG. 5B is a cross-sectional view of the backing layer 100 formed by arranging the backing elements 10 illustrated at (a) of FIG. 5A in a one-dimensional manner, and (c) of FIG. 5B is a cross-sectional view of the backing layer 100 formed by arranging the backing elements 10 illustrated at (a) of FIG. 5B in a two-dimensional manner. The linear line illustrated with dotted line on FIG. 5B is referred to as a dicing line 'L'. At a domain (a curvature domain illustrated with dotted line at the (c) of FIG. 5B, that is, a "B" domain) divided by the dicing line 'L', one ultrasonic transducer element is connected.

When comparing a case of forming the backing layer 100 by arranging the members 11 having a shape of a hexagonal column in a two-dimensional manner while the each of the members 11 is provided with the conductive trace 12 formed only at one side surface thereof (refer to (c) of FIG. 5A) to a case of forming the backing layer 100 by arranging the members 11 having a shape of a hexagonal column in a two-dimensional manner while the each of the members 11 is provided with the conductive trace 12 formed at two side surfaces thereof (refer to (c) of FIG. 5B), with respect to the thickness of the conductive trace 12 of the "A" domain illustrated on (c) of FIG. 5A, the thickness of the conductive trace 12 of the "B" domain illustrated on (c) of FIG. 5B becomes thicker by about twice. As the above, when the thickness of the conductive trace 12 being electrically connected to one ultrasonic transducer element becomes thicker, the electrical characteristic of the conductive trace 12 may be further enhanced.

Figure 6A:
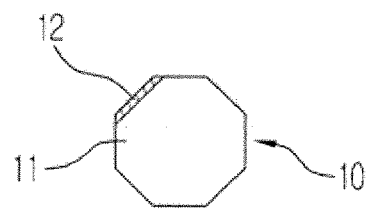
FIG. 6A is a cross-sectional view provided to describe a backing element of an ultrasonic probe in accordance with the third embodiment of the present disclosure in a case when a conductive trace is formed only at one side surface of the member having a shape of a polygonal (octagonal) column that forms the backing element of the ultrasonic probe, the backing layer of the ultrasonic probe formed by arranging the backing elements of the ultrasonic probe in a one-dimensional manner, and the backing layer of the ultrasonic probe formed by arranging the backing elements of the ultrasonic probe in a two-dimensional manner.
Figure 6A:
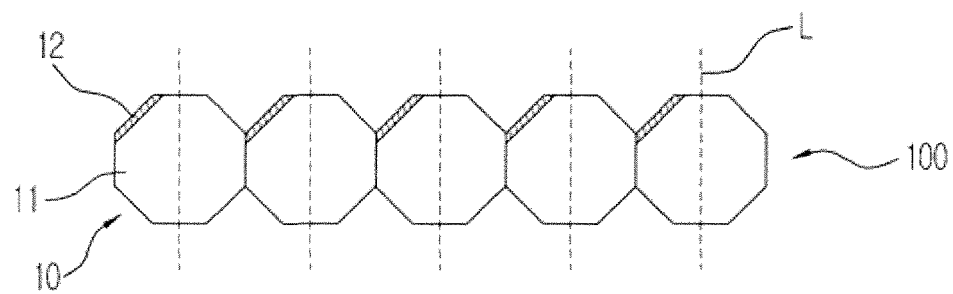
Figure 6A:
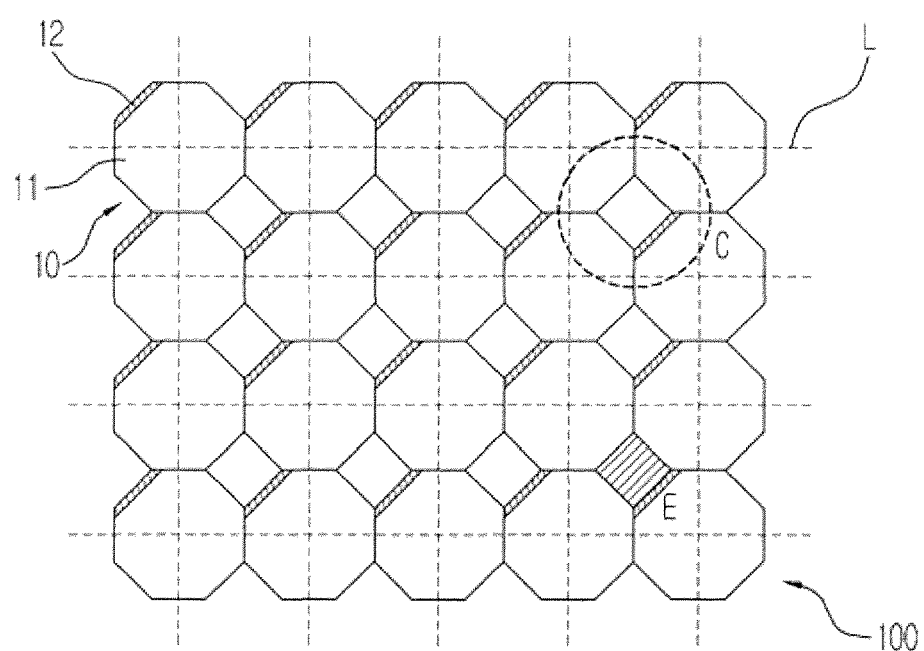

(a) of FIG. 6A is a cross-sectional view of the backing element 10 having the member 11 having a shape of a polygonal (octagonal) column and the conductive trace 12 formed at one side surface of the member 11 having a shape of an octagonal column, (b) of FIG. 6A is a cross-sectional view of the backing layer 100 formed by arranging the backing elements 10 illustrated at (a) of FIG. 6A in a one-dimensional manner, and (c) of FIG. 6A is a cross-sectional view of the backing layer 100 formed by arranging the backing elements 10 illustrated at the (a) of FIG. 6A in a two-dimensional manner. The linear line illustrated with dotted line on FIG. 6A is referred to as a dicing line 'L'. At a domain (a curvature domain illustrated with dotted line at (c) of FIG. 6A, that is, the "C" domain) divided by the dicing line 'L', one ultrasonic transducer element is connected.

Figure 6B:
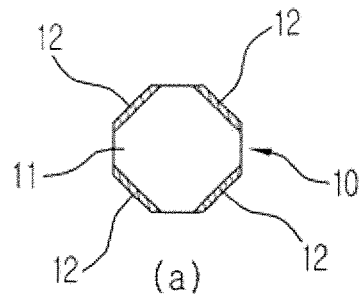
FIG. 6B is a cross-sectional view provided to describe the backing element of the ultrasonic probe in accordance with the third embodiment of the present disclosure in a case when conductive traces are formed at four side surfaces of the member having a shape of a polygonal (octagonal) column that forms the backing element of the ultrasonic probe, the backing layer of the ultrasonic probe formed by arranging the backing elements of the ultrasonic probe in a one-dimensional manner, and the backing layer of the ultrasonic probe formed by arranging the backing element of the ultrasonic probe in a two-dimensional manner.
Figure 6B:
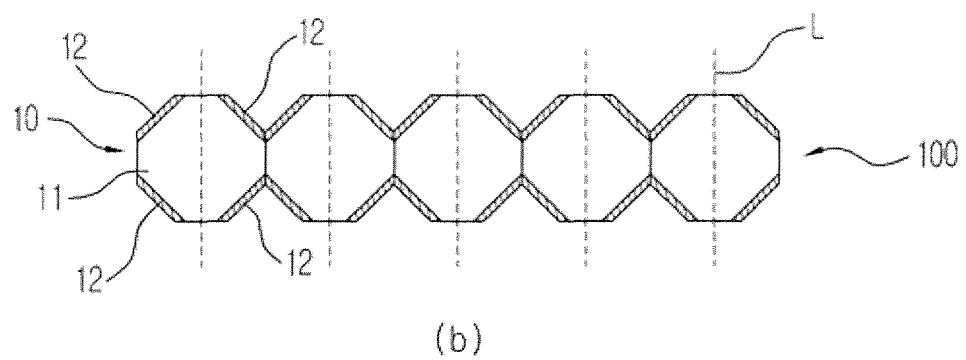
Figure 6B:
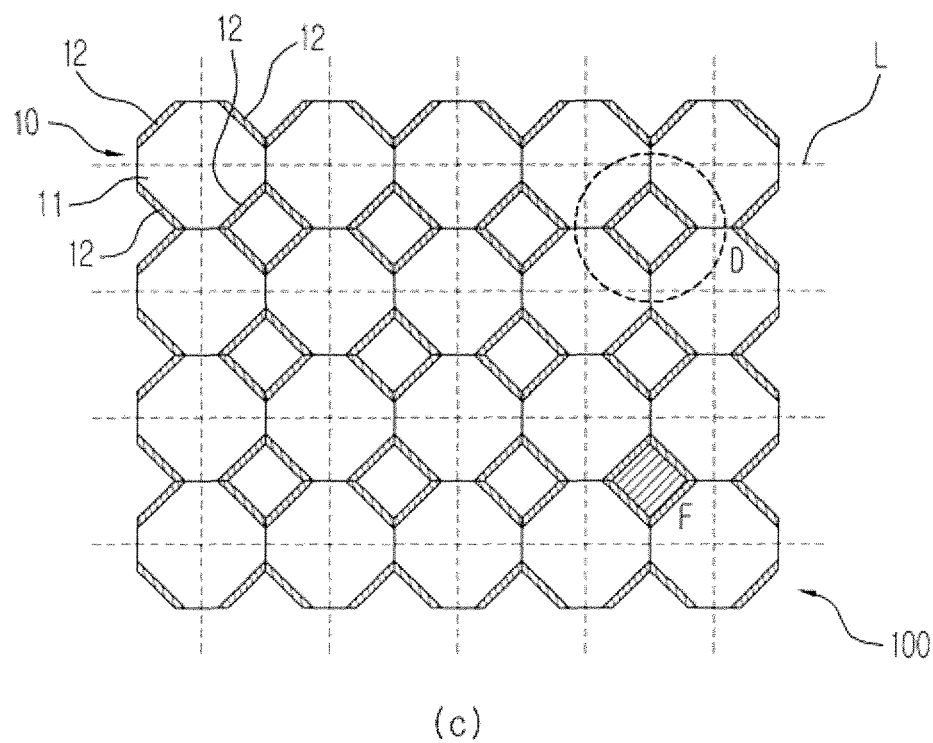

(a) of FIG. 6B is a cross-sectional view of the backing element 10 having the member 11 having a shape of a polygonal (octagonal) column and the conductive traces 12 formed at four side surfaces of the member 11 having a shape of an octagonal column, (b) of FIG. 6B is a cross-sectional view of the backing layer 100 formed by arranging the backing elements 10 illustrated at (a) of FIG. 6A in a one-dimensional manner, and (c) of FIG. 6B is a cross-sectional view of the backing layer 100 formed by arranging the backing elements 10 illustrated at (a) of FIG. 6B in a two-dimensional manner. The linear line illustrated with dotted line on FIG. 6B is referred to as a dicing line 'L'. At a domain (a curvature domain illustrated with dotted line at (c) of FIG. 6B, that is, the "D" domain) divided by the dicing line 'L', one ultrasonic transducer element is connected.

When comparing a case of forming the backing layer 100 by arranging the members 11 having a shape of an octagonal column in a two-dimensional manner while each member 11 is provided with the conductive trace 12 formed only at one side surface thereof (refer to (c) of FIG. 6A) to a case of forming the backing layer 100 by arranging the members 11 having a shape of an octagonal column in a two-dimensional manner while each member 11 is provided with the conductive trace 12 formed at four side surfaces thereof (refer to (c) of FIG. 6B), with respect to the conductive trace 12 being present at the "C" domain illustrated on (c) of FIG. 6A, the conductive trace 12 being present at the "D" domain illustrated on (c) of FIG. 6B is greater by about four times. As the above, when the amount of the conductive trace 12 being electrically connected to one ultrasonic transducer element is increased, the electrical characteristic of the conductive trace 12 may be further enhanced.

Meanwhile, in a case of forming the backing layer 100 by arranging the members 11 having a shape of an octagonal column in a two-dimensional manner while each member 11 is provided with the conductive trace 12 formed only at one side surfaces thereof (refer to (c) of FIG. 6A) or in a case of forming the backing layer 100 by arranging the members 11 having a shape of an octagonal column in a two-dimensional manner while each member 11 is provided with the conductive trace 12 formed at four side surfaces thereof (refer to (c) of FIG. 6B), at each of an in-between of the arrangements of the members 11 having a shape of an octagonal column, empty spaces (the "E" domain of (c) of FIG. 6A and the "F" domain of (c) of FIG. 6B) are being generated. The backing layer 100 is needed to perform a function to prevent an image distortion by blocking an ultrasonic wave being proceeded toward a rear of the piezo-electric layer, and when an empty space is present at an inside the backing layer 100, the backing performance of the backing layer 100 may be reduced. Thus, in addition to a case when an empty space is generated in between the arrangements of the members having a shape of an octagonal column, as in the case of the two-dimensional arrangement of the members 11 having a shape of an octagonal column, also in a case when a visible empty space is not generated at each of an in-between of the arrangements of the members having a shape of a hexagonal column, as in the case of the two-dimensional arrangement of the members having a shape of a hexagonal column, the plurality of members provided with various shapes of polygonal column thereof may be adhesively attached to each other by using the same material as the material of the members when arranging the plurality of members provided with various shapes of polygonal column thereof in a one-dimensional manner or in a two-dimensional manner, and thus the valid area of the backing layer 100 may be increased.

Figure 7:
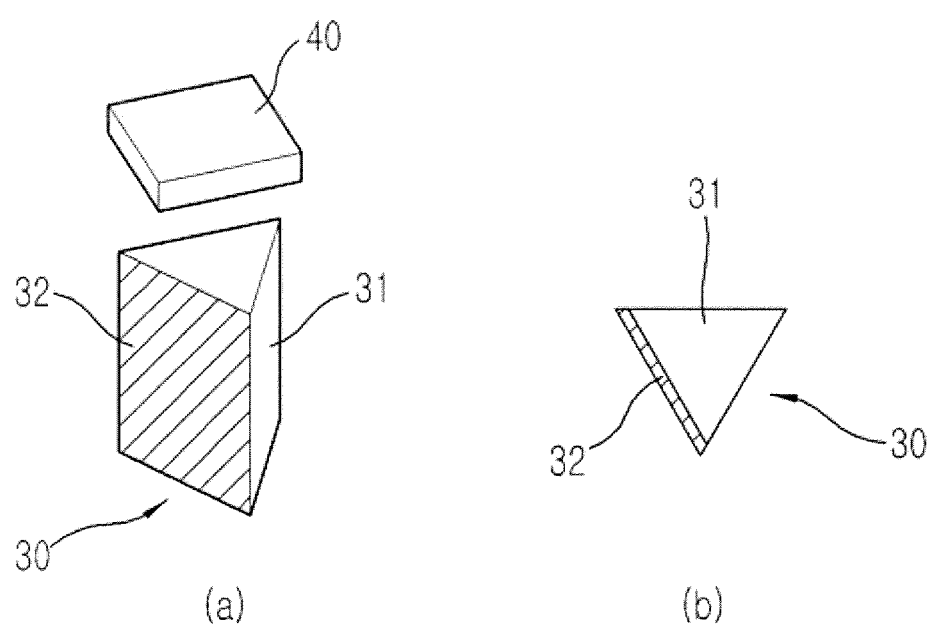
FIG. 7 illustrates a perspective view and a cross-sectional view of a backing element of an ultrasonic probe in accordance with the fourth embodiment of the present disclosure.

FIG. 7 illustrates a perspective view and a cross-sectional view of a backing element of an ultrasonic probe in accordance with the fourth embodiment of the present disclosure.

As illustrated on (a) of FIG. 7, a backing element 30 of an ultrasonic probe in accordance with the fourth embodiment of the present disclosure includes a member 31 having a shape of a polygonal column and a conductive trace 32 formed at one side surface of the member 31. On FIG. 7, as the member having a shape of a polygonal column, the member 31 having a shape of a triangular column from various polygonal columns is provided as an example.

The backing element 30 illustrated on (a) of FIG. 7, becomes a basic component of a backing layer that is configured to absorb an ultrasonic wave that is radiated toward a rear of the piezo-electric layer by the resonance of a piezo-electric element (oscillator) that composes the piezo-electric layer at an inside a transducer module. Here, the member 31 having a shape of a polygonal column is manufactured by synthetic material composed of epoxy resin, tungsten, and rubber powder, and other than the synthetic material as such, any material suitable for absorbing rear sound caused by the resonance of piezo-electric material may be used in manufacturing the member 31 having a shape of a polygonal column.

As illustrated on (a) of FIG. 7, at one side surface of the member 31 having a shape of a triangular column while provided with three units of side surfaces thereof, a conductive trace 32 is formed. Here, the forming of the conductive trace 32 is referred to as the adding (plastering) electrical contact point material on a side surface of the member 31 having a shape of a polygonal column by using various adjustment synthesis techniques. When forming the conductive trace 32, as the electrical contact point material, metals, graphite of conductive material, or conductive ink may be used, and as a method of adding electrical contact point material on a side surface of the member 31 having a shape of a polygonal column, a technique such as a laser scribing, a planting, a deposition, or a printing may be applied.

The backing element 30 is electrically and acoustically connected to one ultrasonic transducer element 40. The ultrasonic transducer element 40 is generally composed of PZT (Lead Zirconium Titanite Ceramics) or a MUT (Micromachined Ultrasonic Transducer). As to describe the electrical and acoustic connection between the backing element 30 and the ultrasonic transducer element 40 in more detail, the member 31 that composes the backing element 30 while having a shape of a polygonal column is acoustically connected to the one ultrasonic transducer element 40 by making contact with the one ultrasonic transducer element 40, and weakens or absorbs acoustic energy that is being radiated from a rear surface of the ultrasonic transducer element 40. In addition, the conductive trace 32 formed at one side surface of the member 31 having a shape of a polygonal column is electrically connected to the one ultrasonic transducer element 40, and electrically connects the ultrasonic transducer element 40.

(b) of FIG. 7 shows a cross section of the backing element 30, and illustrates an image of the conductive trace 32 formed only at one side surface of the member 11 having a shape of a triangular column provided with three units of side surfaces thereof.

Figure 8:
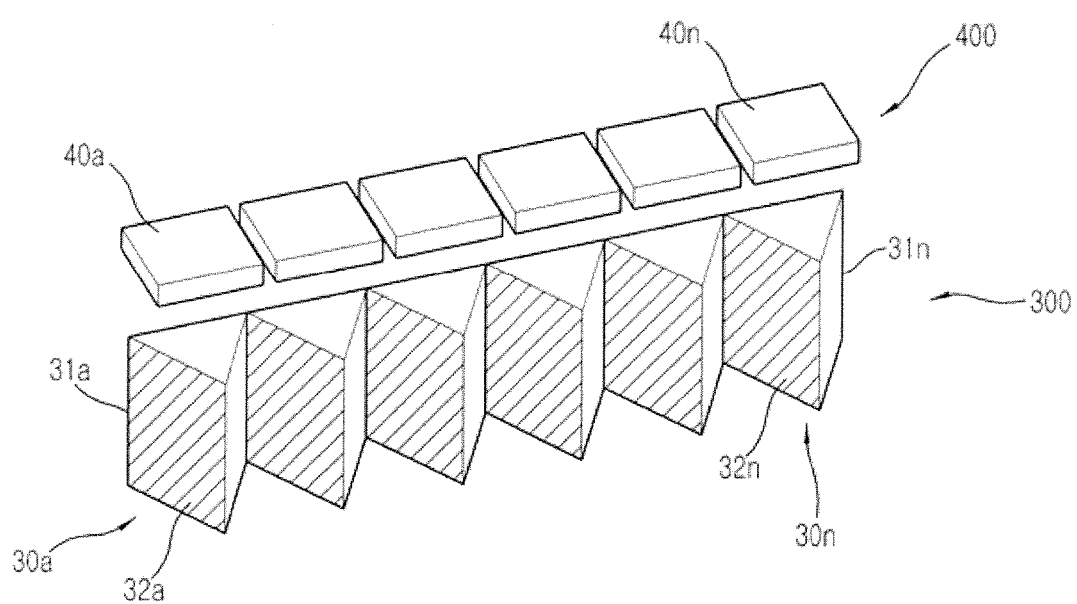
FIG. 8 is a perspective view of a backing layer of the ultrasonic probe formed by arranging the backing elements of the ultrasonic probe in a one-dimensional manner in accordance with the fourth embodiment of the present disclosure.

FIG. 8 is a perspective view of a backing layer of the ultrasonic probe formed by arranging the backing elements of the ultrasonic probe in a one-dimensional manner in accordance with the fourth embodiment of the present disclosure.

The backing element 30, which is same as the backing element 30 illustrated on (a) of FIG. 7, is provided in plurality units (a 'n' number of the backing element 30), and by arranging a plurality of backing elements 30a to 30n in a one-dimensional manner, that is, in a linear manner, a backing layer 300 is formed as illustrated on FIG. 8.

As illustrated on FIG. 8, at the backing layer 300 formed by arranging the plurality (the 'n' number) of the backing elements 30a to 30n in a one-dimensional manner, a one-dimensional ultrasonic transducer array 400 formed by arranging a plurality (a 'n' number) of ultrasonic transducer elements 40a to 40n in a one-dimensional manner is electrically and acoustically connected. As to describe the electrical and acoustic connection between the backing layer 300 and the one-dimensional ultrasonic transducer array 400 in detail, members 31a to 31n having a shape of a polygonal column that compose the backing layer 300 are acoustically connected to the one-dimensional ultrasonic transducer array 400 by making contact with the one-dimensional ultrasonic transducer array 400, and weakens or absorbs acoustic energy that is being radiated from a rear surface of the one-dimensional ultrasonic transducer array 400. In addition, conductive traces 32a to 32n each formed at each of the members 31a to 31n having a shape of a polygonal column is electrically connected to one of the plurality (the 'n' number) of the ultrasonic transducer elements that composes the one-dimensional ultrasonic transducer array 400, and electrically connects the ultrasonic transducer elements 40a to 40n. Although not illustrated on FIG. 8, the backing layer 300 of the ultrasonic probe is mounted at a printed circuit board (not shown), and the conductive traces 32a to 32n each formed at each of the members 31a to 31n having a shape of a polygonal column forming the backing layer 300 is electrically connected to a conductive trace formed at the printed circuit board, and electrically connects each of the ultrasonic transducer elements 40a to 40n.

Figure 9:
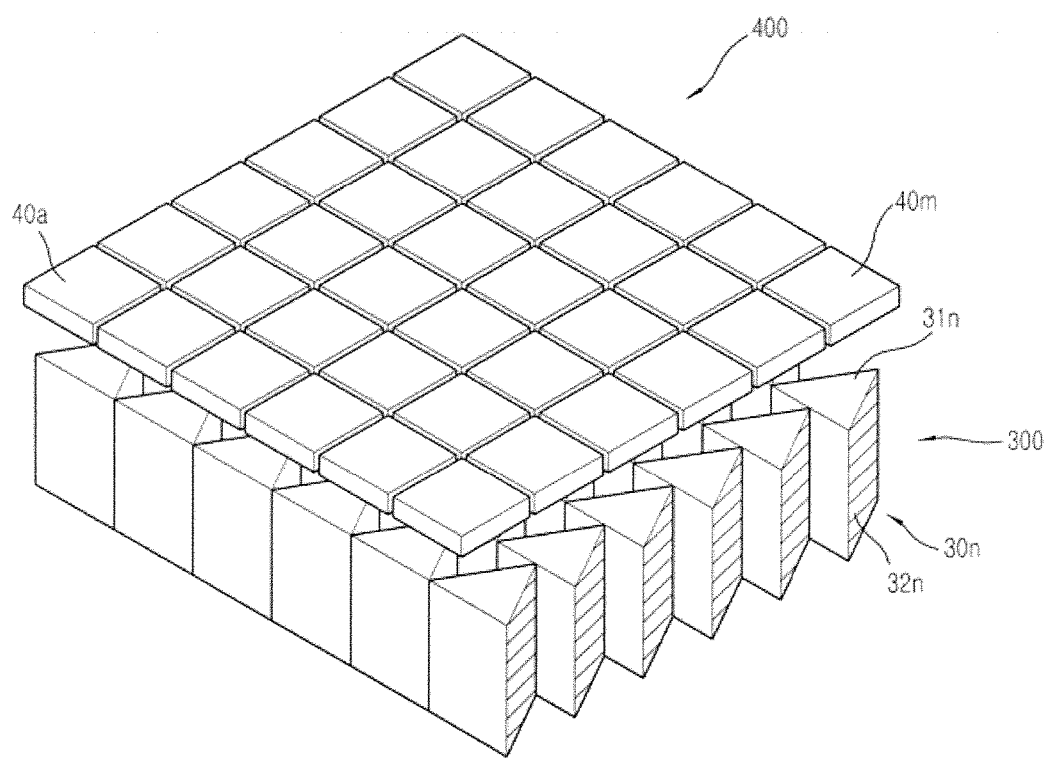
FIG. 9 is a perspective view of a backing layer of the ultrasonic probe formed by arranging the backing elements of the ultrasonic probe in a two-dimensional manner in accordance with the fourth embodiment of the present disclosure.

FIG. 9 is a perspective view of a backing layer of the ultrasonic probe formed by arranging the backing elements of the ultrasonic probe in a two-dimensional manner in accordance with the fourth embodiment of the present disclosure.

The backing element 30, which is same as the backing element 30 illustrated on (a) of FIG. 7, is provided in plurality units (a 'n' number of the backing element 30), and by arranging a plurality of backing elements 30a to 30n in a two-dimensional manner, that is, in a plane manner, a backing layer 300 is formed as illustrated on FIG. 9.

As illustrated on FIG. 9, a two-dimensional ultrasonic transducer array 400 formed by arranging a plurality (a 'm' number) of ultrasonic transducer elements 20a to 20m in a two-dimensional manner is electrically and acoustically connected to the backing layer 300 formed by arranging the plurality (the 'n' number) of the backing elements 30a to 30n in a two-dimensional manner. As to describe the electrical and acoustic connection between the backing layer 300 and the two-dimensional ultrasonic transducer array 400 in more detail, the plurality of members 31a to 31n having a shape of a polygonal column that compose the backing layer 300 are acoustically connected to the two-dimensional ultrasonic transducer array 400 by making contact with the two-dimensional ultrasonic transducer array 400, and weakens or absorbs acoustic energy that is being radiated from a rear surface of the two-dimensional ultrasonic transducer array 400. In addition, conductive traces 32a to 32n each formed at each of the plurality of members 31a to 31n having a shape of a polygonal column is electrically connected to one of the plurality (the 'm' number) of the ultrasonic transducer elements that forms the two dimensional ultrasonic transducer array 400, and electrically connects the ultrasonic transducer elements 40a to 40m. Although not illustrated on FIG. 9, the backing layer 300 of the ultrasonic probe is mounted at a printed circuit board (not shown), and the conductive traces 32a to 32n each formed at each of the members 31a to 31n having a shape of a polygonal column forming the backing layer 300 is electrically connected to a conductive trace formed at the printed circuit board, and electrically connects each of the ultrasonic transducer elements 40a to 40m.

Figure 10:
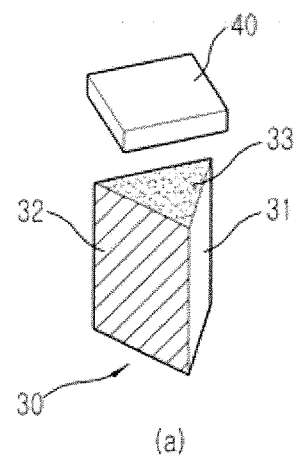
FIG. 10 illustrates a perspective view of a backing element of an ultrasonic probe in accordance with the fifth embodiment of the present disclosure, and a perspective view of a backing layer of the ultrasonic probe formed by arranging the backing elements of the ultrasonic probe in a one-dimensional manner in accordance with the fifth embodiment of the present disclosure.
Figure 10:
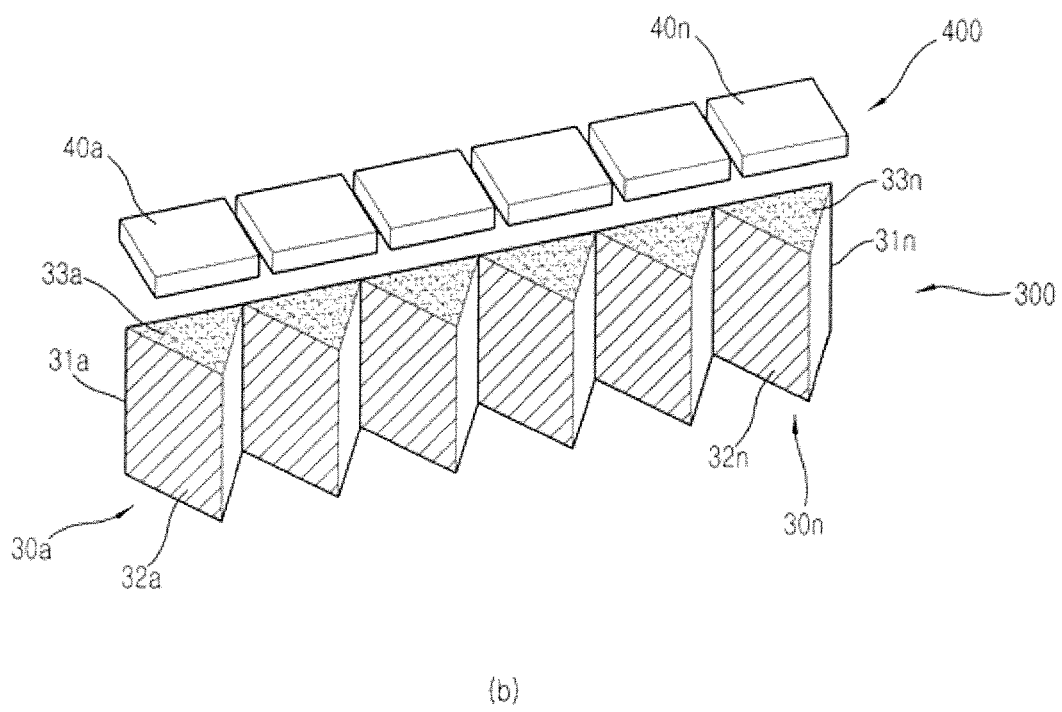

FIG. 10 illustrates a perspective view of a backing element of an ultrasonic probe in accordance with the fifth embodiment of the present disclosure, and a perspective view of a backing layer of the ultrasonic probe formed by arranging the backing elements of the ultrasonic probe in a one-dimensional manner in accordance with the fifth embodiment of the present disclosure.

As illustrated on (a) of FIG. 10, the backing element 30 of the ultrasonic probe in accordance with the fifth embodiment of the present disclosure, which is provided with an electrode layer 33 further formed at an upper surface or at a lower surface of the member 31 having a shape of a polygonal column being acoustically connected to the ultrasonic transducer element 40, is different from the backing element 30 illustrated on (a) of FIG. 7. As the above, when the electrode layer 33 is formed at an upper surface or at a lower surface of the member 31 having a shape of a polygonal column being acoustically connected to the ultrasonic transducer element 40, the electrical connection between the ultrasonic transducer element 40 and the conductive trace 32 formed at a side surface of the member 31 having a shape of a polygonal column may be further enhanced.

The backing element 30, which is same as the backing element 30 illustrated on (a) of FIG. 10, is provided in plurality units (a 'n' number of the backing element 30), and by arranging a plurality of backing elements 30a to 30n in a one-dimensional manner, that is, in a linear manner, the backing layer 300 is formed as illustrated on (b) of FIG. 10.

With respect to the structure of a circuit of the backing layer 300 of the ultrasonic probe formed by arranging the backing elements of the ultrasonic probe in a one-dimensional manner in accordance with the fifth embodiment of the present disclosure as illustrated on (b) of FIG. 10, other than the structure of the electrode layer 33 formed at an upper surface or at a lower surface of the member 31 having a shape of a polygonal column, since all other components are same as the structure of the backing layer 300 of the ultrasonic probe formed by arranging the backing elements of the ultrasonic probe in a one-dimensional manner in accordance with the fourth embodiment of the present disclosure as illustrated on FIG. 7, the detailed description as such will be omitted.

Figure 11A:
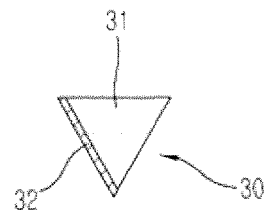
FIG. 11A is a cross-sectional view provided to describe the backing element of the ultrasonic probe in accordance with the fourth embodiment of the present disclosure in a case when a conductive trace is formed only at one side surface of the member having a shape of a polygonal (triangular) column that forms the backing element of the ultrasonic probe, the backing layer of the ultrasonic probe formed by arranging the backing elements of the ultrasonic probe in a one-dimensional manner, and the backing layer of the ultrasonic probe formed by arranging the backing elements of the ultrasonic probe in a two-dimensional manner.
Figure 11A:
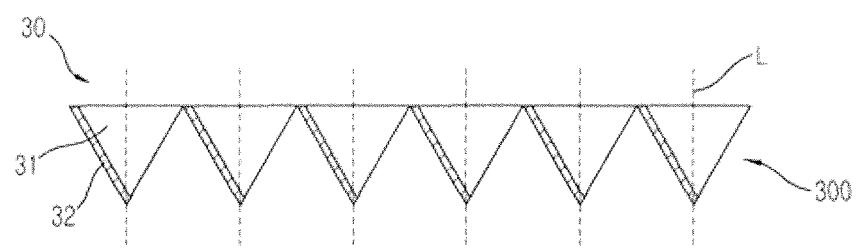
Figure 11A:
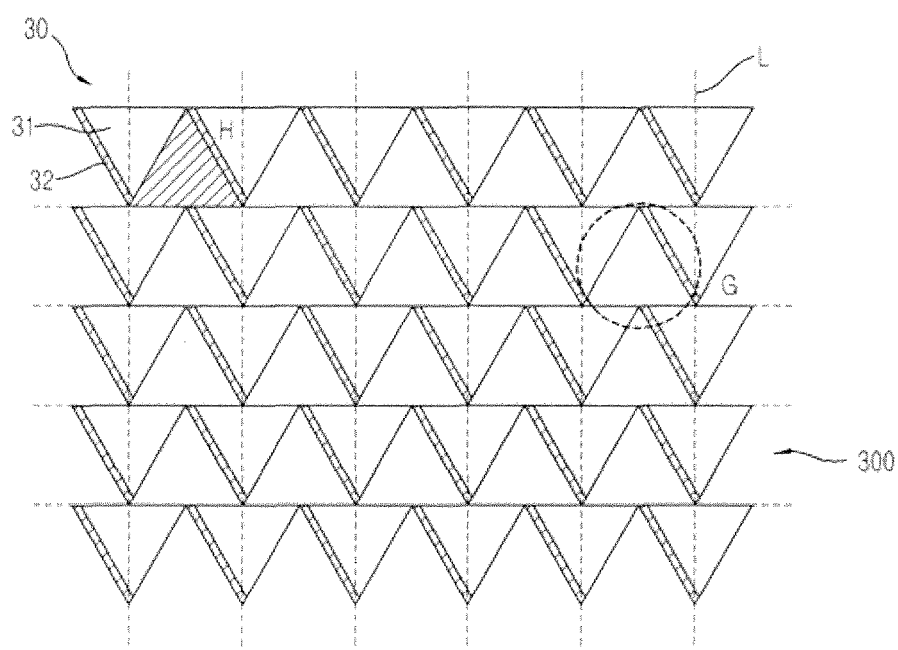

(a) of FIG. 11A is a cross-sectional view of the backing element 30 having the member 31 having a shape of a triangular column and the conductive trace 32 formed at one side surface of the member 31 having a shape of a triangular column, (b) of FIG. 11A is a cross-sectional view of the backing layer 300 formed by arranging the backing elements 30 illustrated at (a) of FIG. 11A in a one-dimensional manner, and (c) of FIG. 11A is a cross-sectional view of the backing layer 300 formed by arranging the backing elements 30 illustrated at (a) of FIG. 11A in a two-dimensional manner. The linear line illustrated with dotted line on FIG. 11A is referred to as a dicing line 'L'. At a domain (a curvature domain illustrated with dotted line at (c) of FIG. 11A, that is, the "G" domain) divided by the dicing line 'L', one ultrasonic transducer element is connected.

Meanwhile, in a case of forming the backing layer 300 by arranging the members 31 having a shape of a triangular column in a two-dimensional manner while each member 31 is provided with the conductive trace 32 formed only at one side surfaces thereof (refer to (c) of FIG. 11A), at each of an in-between of the arrangements of the members 31 having a shape of a triangular column, an empty space (the "H" domain of (c) of FIG. 11A) is being generated. The backing layer 300 is needed to perform a function to prevent an image distortion by blocking an ultrasonic wave being proceeded toward a rear of the piezo-electric layer, and when an empty space is present at an inside the backing layer 300, the backing performance of the backing layer 300 may be reduced. Thus, in a case when an empty space is generated in between the arrangements of the members having a shape of a triangular column, as in the case of the two-dimensional arrangement of the members 31 having a shape of a triangular column, the plurality of members provided with various shapes of polygonal column thereof may be adhesively attached to each other by using the same material as the material of the members, so that an empty space "H" may be filled with the same material as the material of the members, and thus the valid area of the backing layer 300 may be increased.

At the above, a case of the forming of the backing layer 300, which is performed by arranging the members 31 having a shape of a polygonal column in a one-dimensional manner or in a two-dimensional manner while each of the members 31 having a shape of a polygonal column is provided with the conductive trace 32 formed only at one side surface thereof, has been described, but hereinafter, by referring to FIG. 11B, a case of the forming of the backing layer 300, which is performed by arranging the members 31 having a shape of a polygonal column in a one-dimensional manner or in a two-dimensional manner while each of the members 31 having a shape of a polygonal column is provided with the conductive traces 32 formed at two side surfaces thereof, will be described.

Figure 11B:
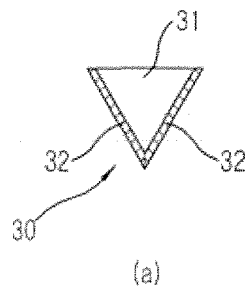
FIG. 11B is a cross-sectional view provided to describe the backing element of the ultrasonic probe in accordance with the fourth embodiment of the present disclosure in a case when conductive traces are formed at two side surfaces of the member having a shape of a polygonal (triangular) column that forms the backing element of the ultrasonic probe, the backing layer of the ultrasonic probe formed by arranging the backing elements of the ultrasonic probe in a one-dimensional manner, and the backing layer of the ultrasonic probe formed by arranging the backing elements of the ultrasonic probe in a two-dimensional manner.
Figure 11B:
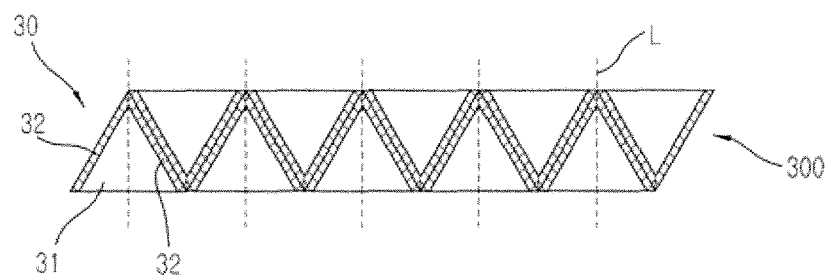
Figure 11B:
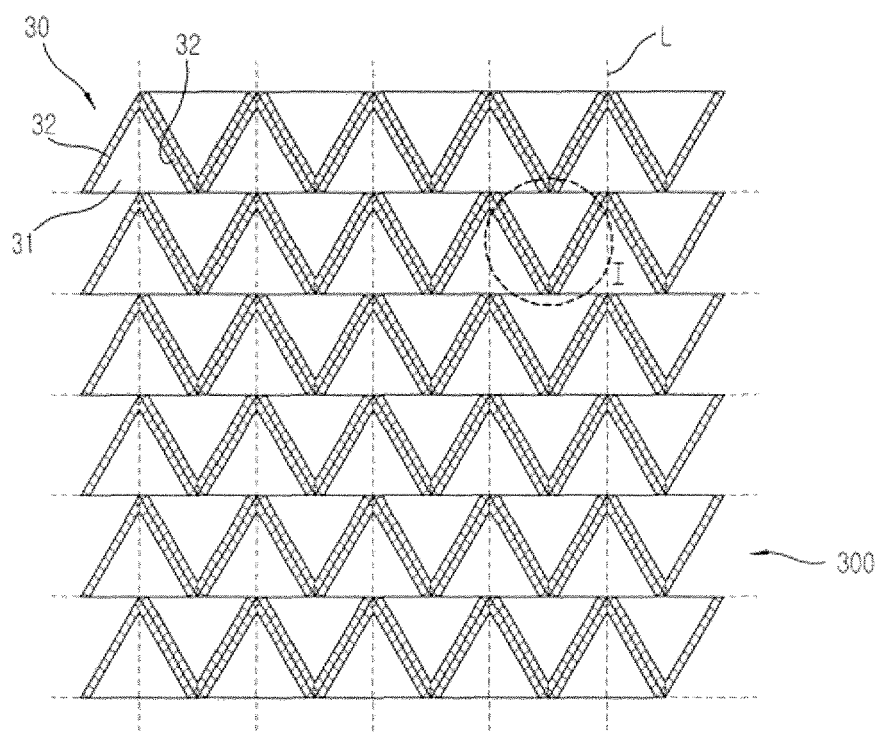

(a) of FIG. 11B is a cross-sectional view of the backing element 30 having the member 31 having a shape of a polygonal (triangular) column and the conductive traces 32 formed at two side surfaces of the member 31 having a shape of a triangular column, (b) of FIG. 11B is a cross-sectional view of the backing layer 300 formed by arranging the backing elements 30 illustrated at (a) of FIG. 11B in a one-dimensional manner, and (c) of FIG. 11B is a cross-sectional view of the backing layer 300 formed by arranging the backing elements 30 illustrated at (a) of FIG. 11B in a two-dimensional manner. The linear line illustrated with dotted line on FIG. 11B is referred to as a dicing line 'L'. At a domain (a curvature domain illustrated with dotted line at (c) of FIG. 11B, that is, the "I" domain) divided by the dicing line one ultrasonic transducer element is connected.

When comparing a case of forming the backing layer 300 by arranging the members 31 having a shape of a triangular column in a two-dimensional manner while each member 31 is provided with the conductive trace 32 formed only at one side surface thereof (refer to (c) of FIG. 11A) to a case of forming the backing layer 300 by arranging the members 31 having a shape of a triangular column in a two-dimensional manner while each member 31 is provided with the conductive traces 12 formed at two side surfaces thereof (refer to (c) of FIG. 11B), with respect to the conductive trace 32 being present at the "G" domain illustrated on (c) of FIG. 11A, the conductive trace 32 being present at the "I" domain illustrated on (c) of FIG. 11B is greater by about four times. As the above, when the amount of the conductive trace 32 being electrically connected to one ultrasonic transducer element is increased, the electrical characteristic of the conductive trace 32 may be further enhanced.

Figure 12A:
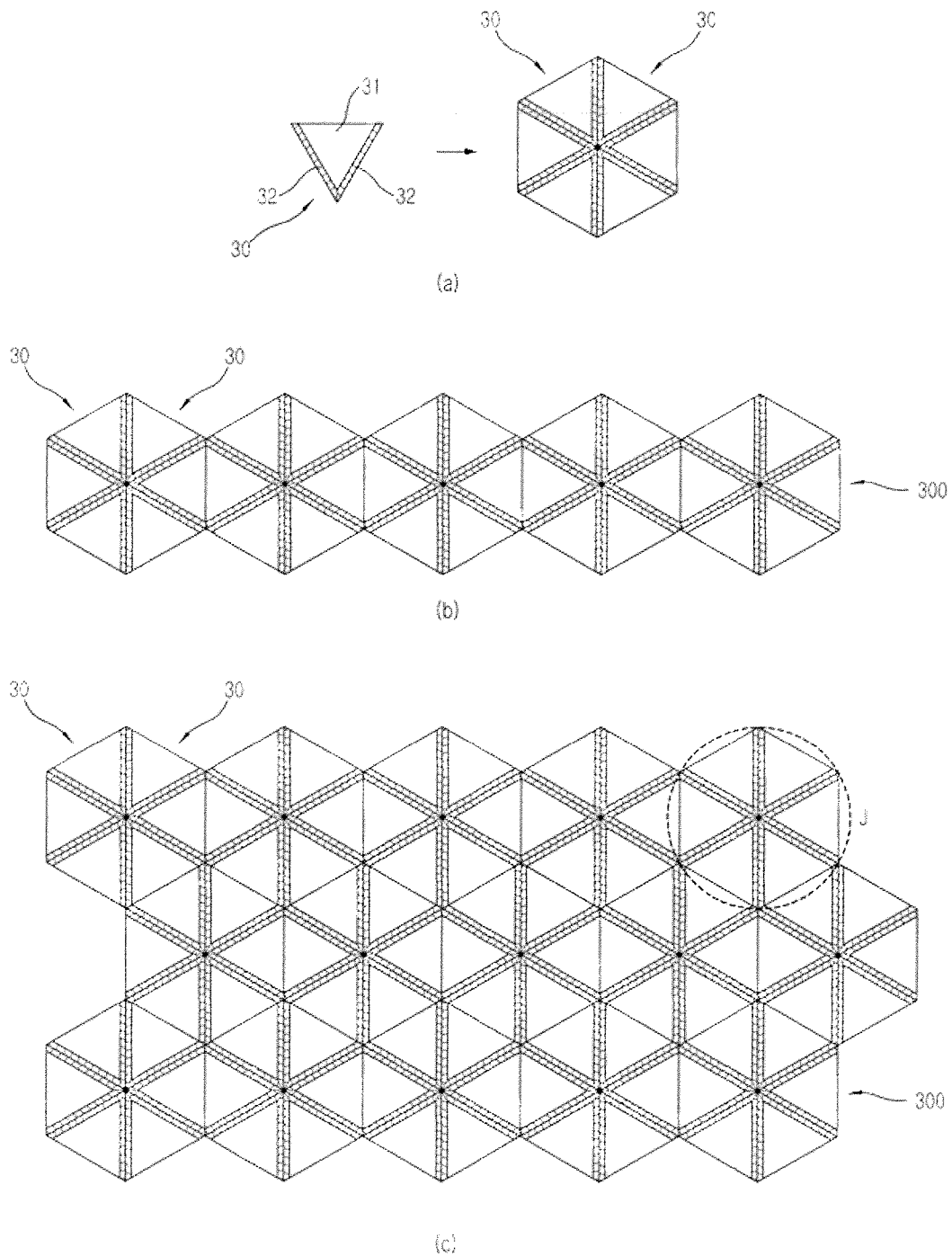
FIG. 12A is a cross-sectional view provided to describe the backing element of the ultrasonic probe in a case when conductive traces are formed at two side surfaces of the member having a shape of a triangular column, the backing element of the ultrasonic probe having a shape of a hexagonal column that is formed by a combination of six of the backing elements, the backing layer of the ultrasonic probe formed by arranging the hexagonal column shape backing elements in a one-dimensional manner, and the backing layer of the ultrasonic probe formed by arranging the hexagonal column shape backing elements in a two-dimensional manner.

(a) of FIG. 12A shows a cross-sectional view of the backing element 30 that includes the member 31 having a shape of a triangular column and also includes the conductive traces 32 formed at two side surfaces of the member 31 having a shape of a triangular column, and also shows a cross-sectional view of a backing element having a shape of a hexagonal column while being formed by a combination of six of the backing elements 30 of the above, (b) of FIG. 12A shows a cross-sectional view of the backing layer 300 formed by arranging the backing elements illustrated at (a) of FIG. 12A in a one-dimensional manner while each of the backing elements is provided with a shape of a hexagonal column, and (c) of FIG. 12A is a cross-sectional view of the backing layer 300 formed by arranging the backing elements 30 illustrated at (a) of FIG. 12A in a two-dimensional manner while each of the backing elements is provided with a shape of a hexagonal column. At a curvature domain (a domain illustrated with dotted line at (c) of FIG. 12A, that is, a "J" domain), one ultrasonic transducer element is connected.

When comparing a case of forming the backing layer 300 by arranging the members 31 having a shape of a triangular column in a two-dimensional manner while each of the members 31 is provided with the conductive trace 32 formed only at one side surface thereof (refer to (c) of FIG. 11A) to a case of forming the backing layer 300 (refer to (c) of FIG. 12A) by arranging the backing elements each formed by a combination of six of the backing elements 30 each having a shape of a triangular column while the backing element is provided with a shape of a hexagonal column (refer to (a) of FIG. 12A), with respect to the conductive trace 32 being present at the "G" domain illustrated on (c) of FIG. 11A, the conductive trace 32 being present at the "J" domain illustrated on (c) of FIG. 12A is greater by about twelve times. As the above, when the amount of the conductive trace 32 being electrically connected to one ultrasonic transducer element is increased, the electrical characteristic of the conductive trace 32 may be further enhanced.

Figure 12B:
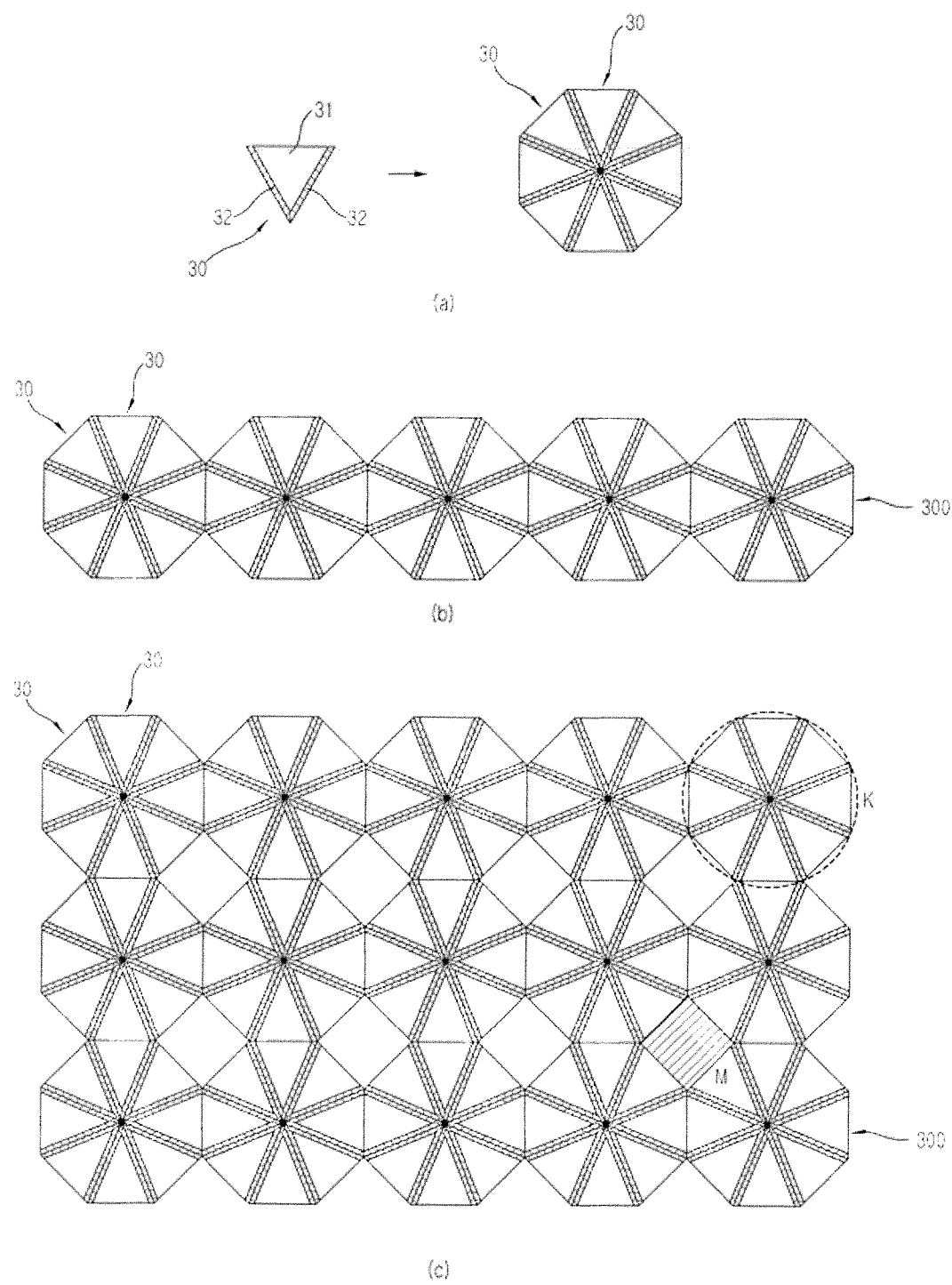
FIG. 12B is a cross-sectional view provided to describe the backing element of the ultrasonic probe in a case when conductive traces are formed at two side surfaces of the member having a shape of a triangular column, the backing element of the ultrasonic probe having a shape of an octagonal column that is formed by a combination of eight of the backing elements, the backing layer of the ultrasonic probe formed by arranging the octagonal column shape backing elements in a one-dimensional manner, and the backing layer of the ultrasonic probe formed by arranging the octagonal column shape backing elements in a two-dimensional manner.

(a) of FIG. 12B shows a cross-sectional view of the backing element 30 that includes the member 31 having a shape of a triangular column and also includes the conductive traces 32 formed at two side surfaces of the member 31 having a shape of a triangular column, and also shows a cross-sectional view of a backing element having a shape of an octagonal column while being formed by a combination of eight of the backing elements 30 of the above, (b) of FIG. 12B is a cross-sectional view of the backing layer 300 formed by arranging the backing elements illustrated at (a) of FIG. 12B in a one-dimensional manner while each of the backing elements is provided with a shape of an octagonal column, and (c) of FIG. 12B is a cross-sectional view of the backing layer 300 formed by arranging the backing elements 30 illustrated at (a) of FIG. 12B in a two-dimensional manner while each of the backing elements is provided with a shape of an octagonal column. At a curvature domain (a domain illustrated with dotted line at t(c) of FIG. 12B, that is, a "K" domain), one ultrasonic transducer element is connected.

When comparing a case of forming the backing layer 300 by arranging the members 31 having a shape of a triangular column in a two-dimensional manner while each of the members 31 is provided with the conductive trace 32 formed only at one side surface thereof (refer to (c) of FIG. 11A) to a case of forming the backing layer 300 (refer to (c) of FIG. 12B) by arranging the backing element formed by a combination of the eight backing elements 30 each having a shape of a triangular column while the backing element is provided with a shape of an octagonal column (refer to (a) of FIG. 12B), with respect to the conductive trace 32 being present at the "G" domain illustrated on (c) of FIG. 11A, the conductive trace 32 being present at the "K" domain illustrated on (c) of FIG. 12B is greater by about sixteen times. As the above, when the amount of the conductive trace 32 being electrically connected to one ultrasonic transducer element is increased, the electrical characteristic of the conductive trace 32 may be further enhanced.

Meanwhile, in a case of forming the backing layer 300 by arranging the backing element in a two-dimensional manner while the backing element is formed by a combination of the eight backing elements 30 each having a shape of a triangular column (refer to (c) of FIG. 12B), at each of an in-between of the arrangements of the backing element each having a shape of an octagonal column, an empty space (a "M" domain of (c) of FIG. 12B) is being generated. The backing layer 300 is needed to perform a function to prevent an image distortion by blocking an ultrasonic wave being proceeded toward a rear of the piezo-electric layer, and when an empty space is present at an inside the backing layer 300, the backing performance of the backing layer 300 may be reduced. Thus, in addition to a case when an empty space is generated in between the arrangements of the backing elements each having a shape of an octagonal column, as in the case of the two-dimensional arrangement of the backing elements each having a shape of an octagonal column, also in a case when a visible empty space is not generated at each of an in-between of the arrangements of the backing elements each having a shape of a hexagonal column, as in the case of the two-dimensional arrangement of the backing elements each having a shape of a hexagonal column, the plurality of members provided with various shapes of polygonal column thereof may be adhesively attached to each other by using the same material as the material of the members when arranging the plurality of members provided with various shapes of polygonal column thereof in a one-dimensional manner or in a two-dimensional manner, and thus the valid area of the backing layer 300 may be increased.

In the present disclosure, examples of forming a backing layer by arranging members each having a shape of a triangular column, a hexagonal column and an octagonal column in a one-dimensional manner or in a two-dimensional manner while each member is provided with a conductive trace formed at one side surface or at more than two side surfaces thereof have been described, but the forming of a backing layer may be possible by arranging members each having various shapes of a polygonal column (for example, a dodecagonal column) other than the shapes above in a one-dimensional manner or in a two-dimensional manner.

In addition, in the present disclosure, examples of forming a backing layer by arranging members having a single shape of a polygonal column (for example, a shape of a triangular column, a shape of a hexagonal column, or a shape of an octagonal column) in a one-dimensional manner or in a two-dimensional manner have been described, but the forming of a backing layer may be possible by combining a one shape of a polygonal column with the other shape of a polygonal column (for example, a combination of the members each having a shape of an octagonal column and the members each having a shape of a rectangular column).

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A backing element of an ultrasonic probe, the backing element comprising:
   a member which is a component of a backing layer having a shape of a polygonal column that is configured to acoustically connect to an ultrasonic transducer element;
   a conductive trace disposed at a first surface of the member and electrically connected to the ultrasonic transducer element; and
   an electrode layer disposed on a second surface of the member, different from the first surface on which the conductive trace is disposed,
   wherein the second surface of the member is acoustically connected to the ultrasonic transducer element,
   the member has a recessed portion on the second surface, the electrode layer being divided by the recessed portion, and
   portions of the electrode layer divided by the recessed portion are electrically connected through the ultrasonic transducer element.

2. The backing element of claim 1, wherein: the conductive trace is disposed at two or more side surfaces of the member.

3. The backing element of claim 2, wherein:
   an electrode layer is disposed on one of an upper surface and a lower surface of the member, and
   the one of the upper surface and the lower surface of the member is acoustically connected to the ultrasonic transducer element.

4. A backing layer of an ultrasonic probe, the backing layer comprising:
   a plurality of members each having a shape of a polygonal column and arranged in a one-dimensional manner or in a two-dimensional manner, each of the plurality of members including a conductive trace on a first surface thereof, wherein:
   the plurality of members are acoustically connected to a ultrasonic transducer array comprising a plurality of ultrasonic transducer elements,
   the conductive trace disposed at each of the plurality of members is electrically connected to one of the plurality of ultrasonic transducer elements, and
   an electrode layer is disposed on a second surface of each of the plurality of members, different from the first surface on which the conductive trace is disposed,
   the electrode layer is acoustically connected to the ultrasonic transducer array,
   each of the plurality of members has a recessed portion on the second surface, the electrode layer being divided by the recessed portion, and
   portions of the electrode layer divided by the recessed portion are electrically connected through the one of the plurality of ultrasonic transducer elements.

5. The backing layer of claim 4, wherein:
   the plurality of members are adhesively attached to each other by using a same material as a material of the plurality of members.

6. The backing layer of claim 4, wherein:
   each of the plurality of members is provided at two or more side surfaces thereof with two or more conductive traces.

7. The backing layer of claim 6, wherein:
   an electrode layer is disposed on one of an upper surface and a lower surface of each of the plurality of members, and
   the one of the upper surface and the lower surface of each of the plurality of members is acoustically connected to the ultrasonic transducer array.

8. The backing layer of claim 6, wherein:
   the plurality of members are adhesively attached to each other by using a same material as a material of the plurality of members.

9. The backing element of claim 1, wherein: the member has a shape of a hexagonal column.

10. The backing element of claim 9, wherein:
    an electrode layer is disposed on one of an upper surface and a lower surface of the member, and
    the one of the upper surface and the lower surface of the member is acoustically connected to the ultrasonic transducer element.

11. The backing element of claim 2, wherein: the member has a shape of a hexagonal column.

12. The backing element of claim 11, wherein:
    an electrode layer is disposed on one of an upper surface and a lower surface of the member, and
    the one of the upper surface and the lower surface of the member is acoustically connected to the ultrasonic transducer element.

13. The backing layer of claim 6, wherein: each of the plurality of members has a shape of a hexagonal column.

14. The backing element of claim 1, wherein: the member has a shape of a triangular column.

15. The backing element of claim 14, wherein:
    an electrode layer is disposed on one of an upper surface and a lower surface of the member, and the one of the upper surface and the lower surface of the member is acoustically connected to the ultrasonic transducer element.

16. The backing element of claim 2, wherein: the member has a shape of a triangular column.

17. The backing element of claim 16, wherein:
an electrode layer is disposed on one of an upper surface and a lower surface of the member, and
the one of the upper surface and the lower surface of the member is acoustically connected to the ultrasonic transducer element.

18. The backing layer of claim 6, wherein: each of the plurality of members has a shape of a triangular column.

19. The backing element of claim 1, wherein:
the one side surface of the member, on which the conductive trace is disposed, is different from the at least one of the upper surface and the lower surface of the member, on which the electrode layer is disposed.

20. The backing element of claim 1, wherein:
the conductive trace is electrically connected to the ultrasonic transducer element through the electrode layer.

* * * * *